US011298065B2

(12) United States Patent
Iyer

(10) Patent No.: US 11,298,065 B2
(45) Date of Patent: Apr. 12, 2022

(54) FETAL HEART RATE EXTRACTION WITHIN A PROCESSOR CONSTRAINED ENVIRONMENT

(71) Applicant: OWLET BABY CARE, INC., Lehi, UT (US)

(72) Inventor: Ajay Sundaram Iyer, Sandy, UT (US)

(73) Assignee: OWLET BABY CARE, INC., Lehi, UT (US)

( * ) Notice: Subject to any disclaimer, the term of this patent is extended or adjusted under 35 U.S.C. 154(b) by 150 days.

(21) Appl. No.: 16/712,284

(22) Filed: Dec. 12, 2019

(65) Prior Publication Data
US 2020/0187804 A1   Jun. 18, 2020

Related U.S. Application Data

(60) Provisional application No. 62/779,014, filed on Dec. 13, 2018.

(51) Int. Cl.
| A61B 5/00 | (2006.01) |
| A61B 5/316 | (2021.01) |
| A61B 5/288 | (2021.01) |
| A61B 5/352 | (2021.01) |

(52) U.S. Cl.
CPC ............ *A61B 5/316* (2021.01); *A61B 5/288* (2021.01); *A61B 5/352* (2021.01); *A61B 5/726* (2013.01)

(58) Field of Classification Search
CPC ......... A61B 5/316; A61B 5/288; A61B 5/352; A61B 5/726; A61B 5/344; A61B 5/7225–7264
See application file for complete search history.

(56) References Cited

U.S. PATENT DOCUMENTS

| 4,781,200 A | 11/1988 | Baker |
| 5,033,864 A | 7/1991 | Lasecki et al. |
| 5,842,982 A | 12/1998 | Mannheimer |
| 5,954,663 A | 9/1999 | Gat |

(Continued)

FOREIGN PATENT DOCUMENTS

| CA | 2885972 | 12/2014 |
| CN | 103260528 | 8/2013 |

(Continued)

OTHER PUBLICATIONS

M.J. Rooijakkers et al. "Influence of Electrode Placement on Signal Quality for Ambulatory Pregnancy Monitoring," Computational and Mathematical Methods in Medicine vol. 2014 pp. 1-12.

(Continued)

*Primary Examiner* — Scott M. Getzow
(74) *Attorney, Agent, or Firm* — Workman Nydegger

(57) ABSTRACT

An abdominal electrocardiogram processing system for determining a fetal heart rate of a fetus in a pregnant woman obtains a combined electrocardiogram measurement of a maternal heart rate and a fetal heart rate. The system then transforms the combined electrocardiogram measurement into a wavelet domain to create a combined electrocardiogram measurement wavelet transform. The system can then remove the maternal heart rate from the combined electrocardiogram measurement wavelet transform. The system then identifies a fetal heart rate from the compensated combined electrocardiogram measurement wavelet transform.

20 Claims, 13 Drawing Sheets

(56) References Cited

U.S. PATENT DOCUMENTS

| | | | |
|---|---|---|---|
| 6,047,201 | A | 4/2000 | Jackson |
| 6,102,856 | A | 8/2000 | Groff et al. |
| 6,454,708 | B1 | 9/2002 | Ferguson et al. |
| 6,498,652 | B1 | 12/2002 | Varshneya et al. |
| 6,569,095 | B2 | 5/2003 | Eggers |
| 7,949,389 | B2 | 5/2011 | Wolfberg et al. |
| 8,094,013 | B1 | 1/2012 | Lee et al. |
| 8,275,436 | B2 | 9/2012 | Wang et al. |
| 8,340,748 | B2 | 12/2012 | Kimura et al. |
| 8,347,144 | B2 | 1/2013 | Khalak et al. |
| 8,417,351 | B2 | 4/2013 | Kilger |
| 8,620,448 | B1 | 12/2013 | Delia |
| 8,666,481 | B2 | 3/2014 | Harrold et al. |
| 8,781,847 | B2 | 7/2014 | Simms et al. |
| 9,028,405 | B2 | 5/2015 | Tran |
| 9,314,159 | B2 | 4/2016 | Lyon et al. |
| 9,579,055 | B1 | 2/2017 | Rood et al. |
| 9,585,614 | B2 | 3/2017 | Dugan |
| 9,763,583 | B2 | 9/2017 | Oz et al. |
| 9,763,616 | B2 | 9/2017 | Dugan |
| 2002/0133067 | A1 | 9/2002 | Jackson |
| 2003/0158593 | A1 | 8/2003 | Heilman et al. |
| 2008/0275349 | A1 | 11/2008 | Halperin et al. |
| 2009/0247849 | A1 | 10/2009 | McCutcheon et al. |
| 2010/0168596 | A1 | 7/2010 | Jaeschke et al. |
| 2010/0241018 | A1 | 9/2010 | Vogel |
| 2010/0274104 | A1 | 10/2010 | Khan |
| 2011/0160591 | A1 | 6/2011 | Smith |
| 2011/0288379 | A1 | 11/2011 | Wu |
| 2012/0209088 | A1 | 8/2012 | Romem |
| 2012/0232398 | A1 | 9/2012 | Roham et al. |
| 2012/0232416 | A1 | 9/2012 | Gilham et al. |
| 2012/0253142 | A1 | 10/2012 | Meger et al. |
| 2012/0299732 | A1 | 11/2012 | Vogel |
| 2013/0021154 | A1 | 1/2013 | Solomon et al. |
| 2013/0072765 | A1 | 3/2013 | Kahn et al. |
| 2013/0102856 | A1 | 4/2013 | Wolfberg |
| 2013/0197362 | A1 | 8/2013 | Mittal et al. |
| 2013/0289361 | A1 | 10/2013 | Bridge et al. |
| 2014/0228653 | A1 | 8/2014 | Kiraly et al. |
| 2015/0150538 | A1 | 6/2015 | Reuter et al. |
| 2015/0164438 | A1 | 6/2015 | Halperin et al. |
| 2015/0201846 | A1 | 7/2015 | Maiershon et al. |
| 2015/0250419 | A1 | 9/2015 | Cooper et al. |
| 2016/0081567 | A1 | 3/2016 | Nousiainen et al. |
| 2016/0120500 | A1 | 5/2016 | Myklebust et al. |
| 2016/0157717 | A1 | 6/2016 | Gaster |
| 2016/0183873 | A1 | 6/2016 | Lin et al. |
| 2016/0317091 | A1 | 11/2016 | Olukoya et al. |
| 2017/0127995 | A1 | 5/2017 | Hyde et al. |
| 2017/0127996 | A1 | 5/2017 | Hyde et al. |
| 2017/0127997 | A1 | 5/2017 | Hyde et al. |
| 2017/0265799 | A1 | 9/2017 | Du et al. |

FOREIGN PATENT DOCUMENTS

| | | |
|---|---|---|
| CN | 104382585 | 3/2015 |
| CN | 105997059 | 10/2016 |
| CN | 106999100 | 8/2017 |
| CN | 107260177 | 10/2017 |
| EP | 1432349 | 6/2006 |
| WO | 2004075750 | 9/2004 |
| WO | 2009146181 | 12/2009 |
| WO | 2011039745 | 4/2011 |
| WO | 201252904 | 4/2012 |
| WO | 201359267 | 4/2013 |
| WO | 201402823 | 1/2014 |
| WO | 2014162135 | 10/2014 |
| WO | 2015062851 | 5/2015 |
| WO | 2015082987 | 6/2015 |
| WO | 201667276 | 5/2016 |
| WO | 201793251 | 6/2017 |
| WO | 2017102566 | 6/2017 |
| WO | 2017142277 | 8/2017 |

OTHER PUBLICATIONS

European Search Report issued in Application No. EP17776853 dated Jul. 22, 2019.

International Search Report and Written Opinion issued in PCT/US/0255563 dated Jun. 21, 2017.

U.S. Appl. No. 15/476,295, Jun. 28, 2019, Office Action.

U.S. Appl. No. 15/476,295, Feb. 10, 2020, Office Action.

FETAL HEART RATE EXTRACTION WITHIN A PROCESSOR CONSTRAINED ENVIRONMENT

CROSS-REFERENCE TO RELATED APPLICATIONS

This application claims priority to and the benefit of U.S. Provisional Application Ser. No. 62/779,014 filed Dec. 13, 2018 entitled "FETAL HEART RATE EXTRACTION WITHIN A PROCESSOR CONSTRAINED ENVIRONMENT." The entire content of the aforementioned application is incorporated by reference herein in its entirety.

BACKGROUND

The use of non-invasive health monitoring devices has been a long sought-after market segment. Recently, many consumer wearable devices have incorporated pulse-oximetry as a sensor for gathering biometric data. While pulse-oximetry data can provide several important insights into an individual's health. There is a desire for increased monitoring that provides information beyond what a standard pulse-oximeter is able to provide. For example, standard wrist-worn pulse-oximeters are unable to provide health information regarding a fetus within the womb of a pregnant woman.

One potential means for providing this information is through the use of abdominal electrodes for fetal monitoring. Abdominal electrodes for fetal monitoring are attractive because they are non-invasive and can potentially allow for in-home and ambulatory use. However, the detection of Fetal QRS locations from the abdominal ECG signal is extremely challenging, especially during the antepartum period (20-40 weeks) of the pregnancy. This is due to the low amplitude of the Fetal ECG signal and significant noise contributions from maternal ECG, maternal movements, fetal movements, vernix caseosa layer, and uterine contractions. These factors contribute to an extremely low SNR (Signal-to-Noise-Ratio) for fetal QRS peaks often resulting in FQRS peaks that are not visually identifiable.

Several single-channel algorithms currently exist in the literature for estimating the location of Fetal QRS peaks from the abdominal ECG. These algorithms, however, trade-off accuracy and performance for lower algorithm complexity. The current state-of-the art algorithms require significant processing power and have high-complexity for achieving reasonable detection performance. Despite the high-complexity, these algorithms do not work well for low SNRs (0-6 dB).

Conventional ECG algorithms and systems fail to provide useful accuracy while minimizing the required system resources. In particular, conventional systems require significant processing power that is not compatible with a mobile, low-power platform. Accordingly, there is a need for a system that overcomes technical challenges relating to the excessive processing requirements needed to identify fetal ECG.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

In at least one disclosed embodiment, an abdominal electrocardiogram processing system for determining a fetal heart rate of a fetus in a pregnant woman comprise obtaining a combined electrocardiogram measurement of a maternal heart rate and a fetal heart rate. The combined electrocardiogram measurement is sampled at a first sample rate. The system then transforms the combined electrocardiogram measurement into a wavelet domain to create a combined electrocardiogram measurement wavelet transform. Additionally, the system determines an estimate of the maternal heart rate from the combined electrocardiogram measurement wavelet transform. The system can then remove the maternal heart rate from the combined electrocardiogram measurement wavelet transform using the estimate of the maternal heart rate to create a compensated combined electrocardiogram measurement wavelet transform. In addition, the system identifies a fetal heart rate from the compensated combined electrocardiogram measurement wavelet transform.

Additionally, in at least one embodiment the system can identify the fetal heart rate using a variety of different means. In some embodiments, the means can include one or more of the following. The system can identify at least one fetal wavelet transform modulus maxima in a particular detail level of a wavelet transform of the compensated combined electrocardiogram measurement wavelet transform. The system can then determine one or more fetal features of the at least one fetal wavelet transform modulus maxima. The system can evaluate each fetal feature of the one or more fetal features against one or more predetermined criteria to identify a plurality of candidate fetal peaks. Additionally, the system can determine a set of preliminary fetal peaks using a probabilistic likelihood search of the plurality of candidate fetal peaks. The system can also determine a kurtosis score and a signal score of each preliminary fetal peak in the set of preliminary fetal peaks for a given time step. Further, the system can select a set of final fetal peaks with kurtosis scores in a first predetermined range and signal scores in a second predetermined range. The system can then display an indication of a final fetal heart rate based on the set of final fetal peaks.

In at least one additional disclosed embodiment, an abdominal electrocardiogram processing system for determining a fetal heart rate of a fetus in a pregnant woman comprise obtaining a combined electrocardiogram measurement of a maternal heart rate and a fetal heart rate. The combined electrocardiogram measurement is sampled at a first sample rate. The system then transforms the combined electrocardiogram measurement into a wavelet domain to create a combined electrocardiogram measurement wavelet transform. Additionally, the system determines an estimate of the maternal heart rate from the combined electrocardiogram measurement wavelet transform.

Additionally, in at least one embodiment the system can identify the maternal heart rate using a variety of different means. In some embodiment, the means can include one or more of the following. The system can identify at least one maternal wavelet transform modulus maxima in a first detail level of the combined electrocardiogram measurement wavelet transform. The system can then determine one or more maternal features of the at least one maternal wavelet transform modulus maxima. Additionally, the system can evaluate each maternal feature of the one or more maternal features against one or more predetermined criteria to identify a plurality of candidate maternal peaks. The system can also obtain a set of windowed candidate maternal peaks, where each windowed candidate maternal peak in the set of windowed candidate maternal peaks is a window of a first number of samples around a candidate maternal peak of the plurality of candidate maternal peaks. Additionally, the system determines a set of template matching scores for the set of windowed candidate maternal peaks. Each template matching score of the set of template matching scores is found using a distance metric between each windowed candidate maternal peak of the set of windowed candidate maternal peaks and a maternal heart rate template. The system then determines a set of maternal peaks using a probabilistic likelihood search of the plurality of candidate maternal peaks that is based at least on the set of template matching scores. The system can further update one or more parameters of the maternal heart rate template based at least on the set of maternal peaks to create an updated maternal heart rate template. The system then determines an estimate of the maternal heart rate based on the set of maternal peaks and the updated maternal heart rate template.

The system can then remove the maternal heart rate from the combined electrocardiogram measurement wavelet transform using the estimate of the maternal heart rate to create a compensated combined electrocardiogram measurement wavelet transform. In addition, the system identifies a fetal heart rate from the compensated combined electrocardiogram measurement wavelet transform.

Additionally, in at least one embodiment the system can identify the fetal heart rate using a variety of different means. In some embodiments, the means can include or more of the following. The system can identify at least one fetal wavelet transform modulus maxima in a particular detail level of a wavelet transform of the compensated combined electrocardiogram measurement wavelet transform. The system can then determine one or more fetal features of the at least one fetal wavelet transform modulus maxima. The system can evaluate each fetal feature of the one or more fetal features against one or more predetermined criteria to identify a plurality of candidate fetal peaks. Additionally, the system can determine a set of preliminary fetal peaks using a probabilistic likelihood search of the plurality of candidate fetal peaks. The system can also determine a kurtosis score and a signal score of each preliminary fetal peak in the set of preliminary fetal peaks for a given time step. Further, the system can select a set of final fetal peaks with kurtosis scores in a first predetermined range and signal scores in a second predetermined range. The system can then display an indication of a final fetal heart rate based on the set of final fetal peaks.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the following drawings.

DETAILED DESCRIPTION

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

In at least one embodiment, the proposed system disclosed herein has a significantly lower complexity than current state-of-the-art systems on medium-to-high SNRs. On low SNR signals the proposed systems potentially outperforms the conventional systems. In at least one embodiment, disclosed systems overcome technical challenges related to the detecting fetal ECG within a processor constrained environment.

One of skill in the art will appreciate that the particular inventive selection of various steps and features in a system can have a dramatic impact on the overall system resources required for the system and the resulting accuracy. For example, in at least one embodiment, the ECG signal is transformed into the wavelet domain and all processing is performed within that domain. In contrast, one or more conventional systems may perform multiple transforms during the identification of the fetal ECG.

One will appreciate in view of the disclosure below that some similar processing methods are performed to both the fetal ECG and the maternal ECG. In some cases, for the sake of conciseness, only the fetal processing or only the maternal processing is described. Nonetheless, one having skill in the art will appreciate that the respective examples and figures substantially apply to both fetal and maternal ECG processing.

Figure 1:
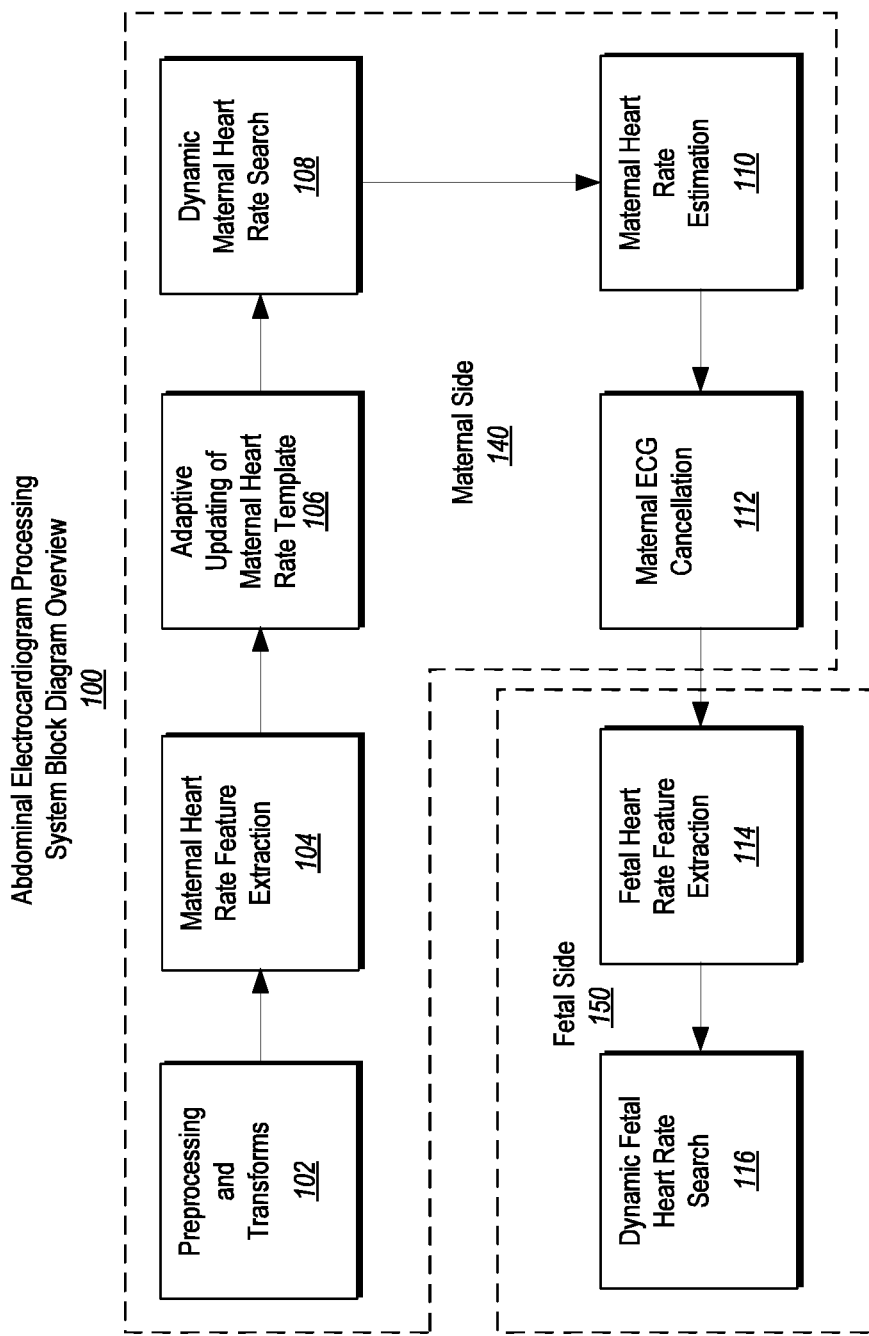
FIG. 1 illustrates on an embodiment of an abdominal electrocardiogram ("ECG" or "AECG") processing system block diagram.

FIG. 1 illustrates an abdominal electrocardiogram ("ECG" or "AECG") processing system block diagram overview 100. This is a simplified block diagram that provides an overview of embodiments of an abdominal ECG processing system. This overview is not intended to describe all details, connections, or signal flows, but rather to describe the general concepts of the abdominal ECG processing system in block diagram form. The signal flow and connections of FIG. 1 should not be seen as limiting other connections, signal flows, operations, or functions of the various blocks in the block diagram. More detail on specific embodiments, functionality of different aspects of the abdominal ECG processing system, and more detailed block diagrams are provided below.

The abdominal ECG processing system block diagram overview 100 consists of two main aspects or sides, a maternal side 140 and a fetal side 150. These two aspects or sides are part of the whole and operate in conjunction to determine or estimate a fetal heart rate from a combined ECG measurement of a maternal heart rate and a fetal heart rate. In some embodiments, this combined measurement is obtained through the use of a bellyband device, such as that depicted in FIG. 2 and discussed below.

The maternal side 140 operates by estimating and canceling the maternal heart rate from the combined ECG measurement. The resulting compensated ECG measurement is then processed by the fetal side 150 to determine or estimate the fetal heart rate.

Turning now to the individual blocks, a combined ECG measurement, comprising a fetal ECG and a maternal ECG, is at a first sample rate. In at least one embodiment, the first sample rate is between 100 Hz and 500 Hz. The combined ECG is subjected to preprocessing and transforms 102. This block prepares the data from the combined ECG measurement and transforms the prepared data into the wavelet domain.

In this stage, the abdominal AECG signal is processed using a Maximal Overlap Discrete Wavelet Transform (MODWT). The MODWT operation is used to decompose the signal into 5 levels, which include 4 detail levels & 1 approximation level. Each level corresponds to a different frequency range as shown below in Table 1.

TABLE 1

| Wavelet Level | Frequency Bandwidth (Hz) |
| --- | --- |
| Detail Level 1 | 50 - 100 Hz |
| Detail Level 2 | 25 - 50 Hz |
| Detail Level 3 | 12.5 - 25 Hz |
| Detail Level 4 | 6.25 - 12.5 Hz |
| Approximation Level 5 | DC - 6.25 Hz |

In at least one embodiment, the Symmlets 4 ('Sym4') wavelet is used as the mother wavelet. Alternatively, a different mother wavelet such as, the debauchies (db6, db20), haar, etc. can be used. The Wavelet Transform (MODWT) may be implemented in the Time-Domain using a filter bank approach. Alternatively, it can also be implemented in the frequency-domain using a fft-convolution approach. It is worth noting that any of these alternative approaches may be used to implement the algorithm and the approach would still be covered under the scope of the invention.

At least one advantage associated with transforming the signal from the time-domain to the wavelet-domain is that it enhances the Signal-To-Noise (SNR) Ratio of the maternal and fetal components of the Abdominal ECG.

Returning to FIG. 1, next is maternal heart rate feature extraction 104. Peaks of the wavelet transform of the combined ECG measurement are found in at least one detail level of the wavelet transform. Features of the peaks are extracted and the features are compared to one or more predetermined criteria. In some embodiments, these predetermined criteria are thresholds on the features. Peaks that meet the one or more predetermined criteria are identified as candidate peaks.

The candidate peaks are then passed to a functional block for adaptive updating of maternal heart rate template 106. In this block, the candidate peaks are compared to a maternal heart rate template using a distance metric. In some embodiments, the distance metric is a normalized Euclidean distance metric. Those skilled in the art are familiar with Euclidean distance metrics and versions of normalized Euclidean distance. However, as used herein, the normalized Euclidean distance metric takes on a specific meaning as a new or improved metric. Further details on the normalized Euclidean distance metric and its definition are provided below.

Adaptive updating of maternal heart rate template 106 uses the final peaks, which are selected or determined at the next block (dynamic heart rate search 108), to update the maternal heart rate template. In some embodiments, updating the maternal heart rate template includes adjusting one or more features of the maternal heart rate template based on the final peaks.

Next, the candidate peaks and their associated distance measures are sent to dynamic heart rate search 108. A probabilistic search is performed which compares likelihoods of a set of candidate peaks being the peaks of the actual maternal heart rate. The distance measures and a maternal heart rate probability density are utilized in the probabilistic search. The best set of candidate peaks is selected as a set of maternal peaks, which are sent to adaptive updating of maternal heart rate template 106, as discussed above.

The set of maternal peaks are sent to maternal heart rate estimation 110, which estimates the maternal heart rate based on the locations of the peaks in the set of maternal peaks and the updated maternal heart rate template.

The estimated maternal heart rate is sent to maternal ECG cancellation 112. Here, the estimated heart rate is subtracted or otherwise cancelled from the combined ECG measurement. The result is a compensated ECG measurement that contains a fetal heart rate ECG measurement.

The compensated ECG measurement is sent from the maternal side 140 to fetal heart rate feature extraction 114 on the fetal side 150. Similar to the maternal heart rate feature extraction 104, the fetal heart rate feature extraction 114 identifies peaks of the wavelet transform of the compensated ECG measurement in at least one detail level of the wavelet transform. Features are then extracted from those peaks and the features are compared to one or more predetermined criteria. In some embodiments, the one or more predetermined criteria are thresholds on the features.

Further, similar to adaptive updating of maternal heart rate template 106, fetal heart rate feature extraction 114 also performs a comparison of the compensated ECG measurement to a fetal heart rate template using a distance metric. In some embodiments, the distance metric is the normalized Euclidean distance metric discussed above and further defined below.

Peaks that meet the one or more predetermined criteria are passed on as candidate peaks with their distance measures to dynamic fetal heart rate search 116. Similar to dynamic heart rate search 108, dynamic fetal heart rate search 116 performs a probabilistic search which compares likelihoods of a set of candidate peaks being the peaks of the actual fetal heart rate. The distance measures and a fetal probability density are utilized in the probabilistic search. The best set of candidate peaks is selected as a preliminary set of fetal peaks.

The fetal probability distribution is updated based on the preliminary set of fetal peaks. In some embodiments, this includes updating the mean of the fetal probability distribution.

The preliminary set of fetal peaks is used with the fetal heart rate template to form a preliminary estimate of the fetal heart rate. The preliminary estimate may be broken up into time steps, where each time step is a portion of the preliminary estimate of the fetal heart rate where a single fetal heart beat should be present. In each time step, each preliminary fetal peak from the preliminary set of fetal peaks is evaluated using one or more scoring criteria. In some embodiments, the one or more scoring criteria include at least a kurtosis score and a signal quality score.

Preliminary fetal peaks which meet one or more predetermined constraints on the one or more scoring criteria are retained, while others are discarded. The result is a final set of fetal peaks that are used to form a final estimate of the fetal heart rate. In some embodiments, the final estimate of the fetal heart rate is the output of the abdominal ECG processing system.

Turning back to the overall abdominal ECG processing system, in some embodiments, a series of combined ECG measurements are made. As each measurement passes through the system, such as according to the block diagram of FIG. 1, the maternal heart rate template, the maternal probability distribution, and the fetal probability distribution are updated and used for the next combined ECG measurement. This allows the abdominal ECG processing system to dynamically update based on the mother's and child's actual heart rates.

Figure 2:
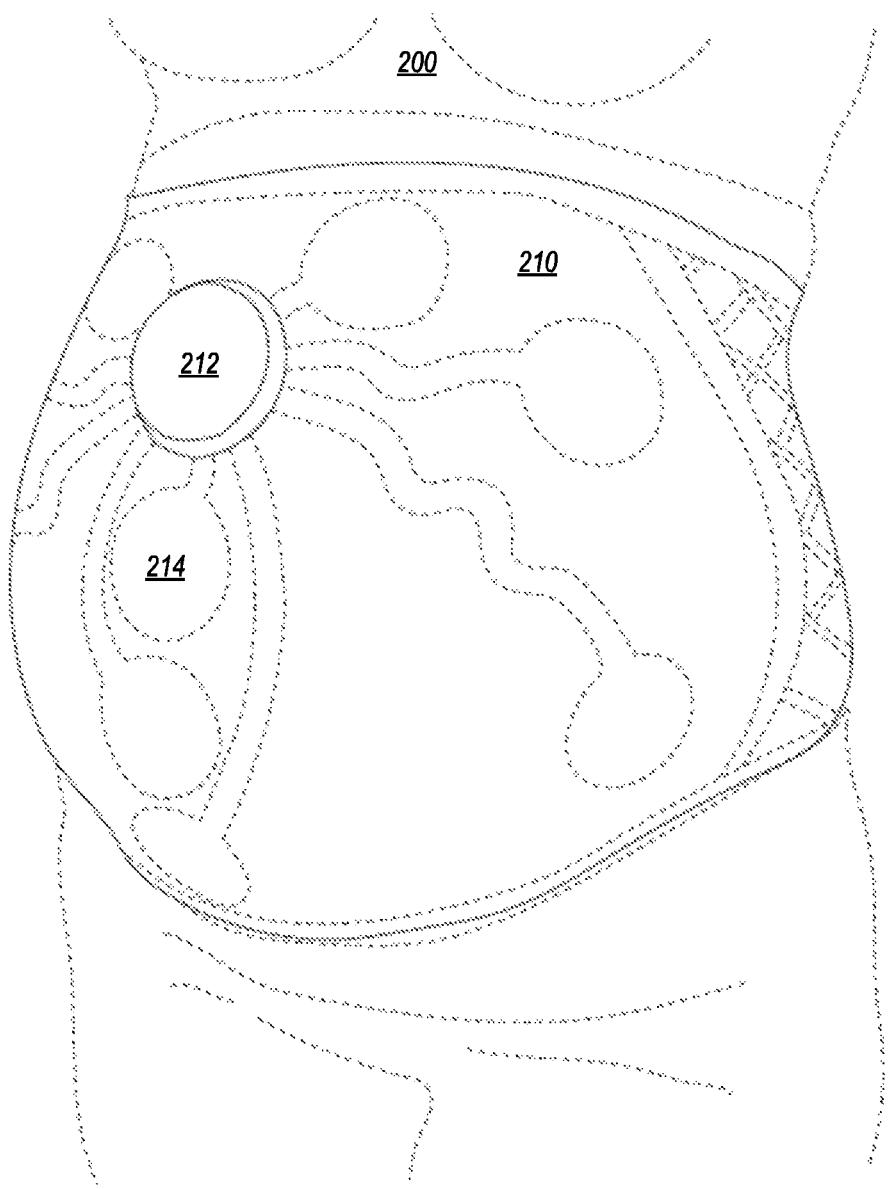
FIG. 2 illustrates an embodiment of a bellyband system.

Attention is now turned to FIG. 2, which presents an example embodiment of a bellyband system 210 with a processing center 212 and a sensor 214. The bellyband system 210 is wrapped around the abdomen of a pregnant woman 200. While FIG. 2 depicts other elements, in embodiments of the present disclosure, only a single sensor 214 is discussed as part of the system.

Processing center 212 receives or accesses ECG measurements from sensor 214 and processes them according to embodiments of an abdominal ECG processing system to determine a fetal heart rate as disclosed herein.

Figure 3:
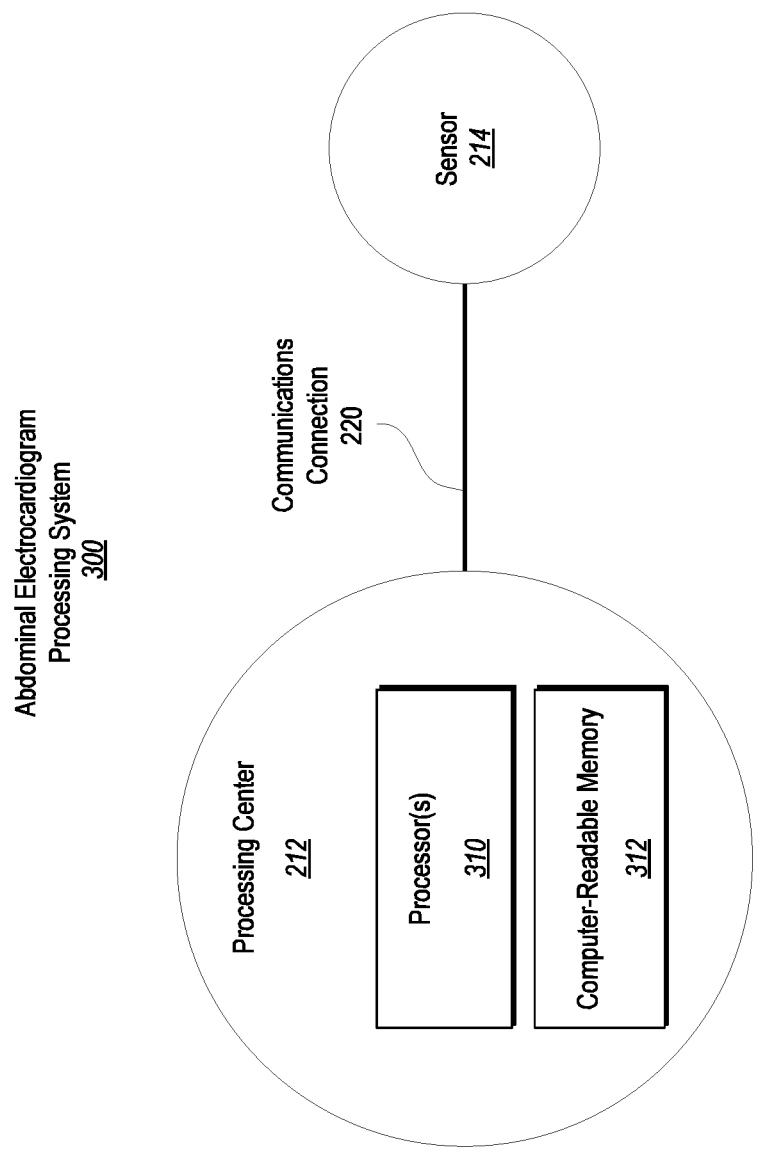
FIG. 3 illustrates an embodiment of an abdominal ECG processing system and provides additional detail on processing center.

FIG. 3 illustrates an embodiment of an abdominal ECG processing system 300 and provides additional detail on processing center 212. Processing center 212 includes processor(s) 310 and computer-readable memory 312. In some embodiments, computer-readable memory 312 contains instructions for determining, calculating, or otherwise finding a fetal heart rate from a combined ECG measurement made by sensor 214, such as according to embodiments of abdominal ECG processing systems described herein. In some embodiments, processor(s) 310 are configured to execute instructions on computer-readable memory 312 to determine, calculate, or otherwise find a fetal heart rate from a combined ECG measurement made by sensor 214, such as according to embodiments of abdominal ECG processing systems described herein.

Sensor 214 is configured to at least measure an ECG from a person to whom sensor 214 is attached. For example, sensor 214 as depicted in FIG. 2 is configured to measure an ECG from a pregnant woman 200 and child.

Processing center 212 is connected to sensor 214 by communications connection 220. Communications connection 220 is configured to provide ECG measurements from sensor 214 to processing center 212. In some embodiments, communications connection 220 is a wired connection, such as a fiber optic cable, Ethernet, a bespoke connector, or other wired connections. In other embodiments, communications connection 220 is a wireless connection, such as wireless internet, Bluetooth, Bluetooth Low Energy, or other wireless connections.

FIGS. 4 through 7 illustrate a number of data plots. The signals in each plot contain peaks that will be referenced and defined in more detail below. Each peak has an amplitude, which is the distance that the peak is located from a time axis. Each peak occurs at a point in time, which is the point where a line drawn vertically from the peak would intersect the time axis. Time differences of peaks will be referred to, which are the differences between the points in time for a pair of peaks.

Figure 4:
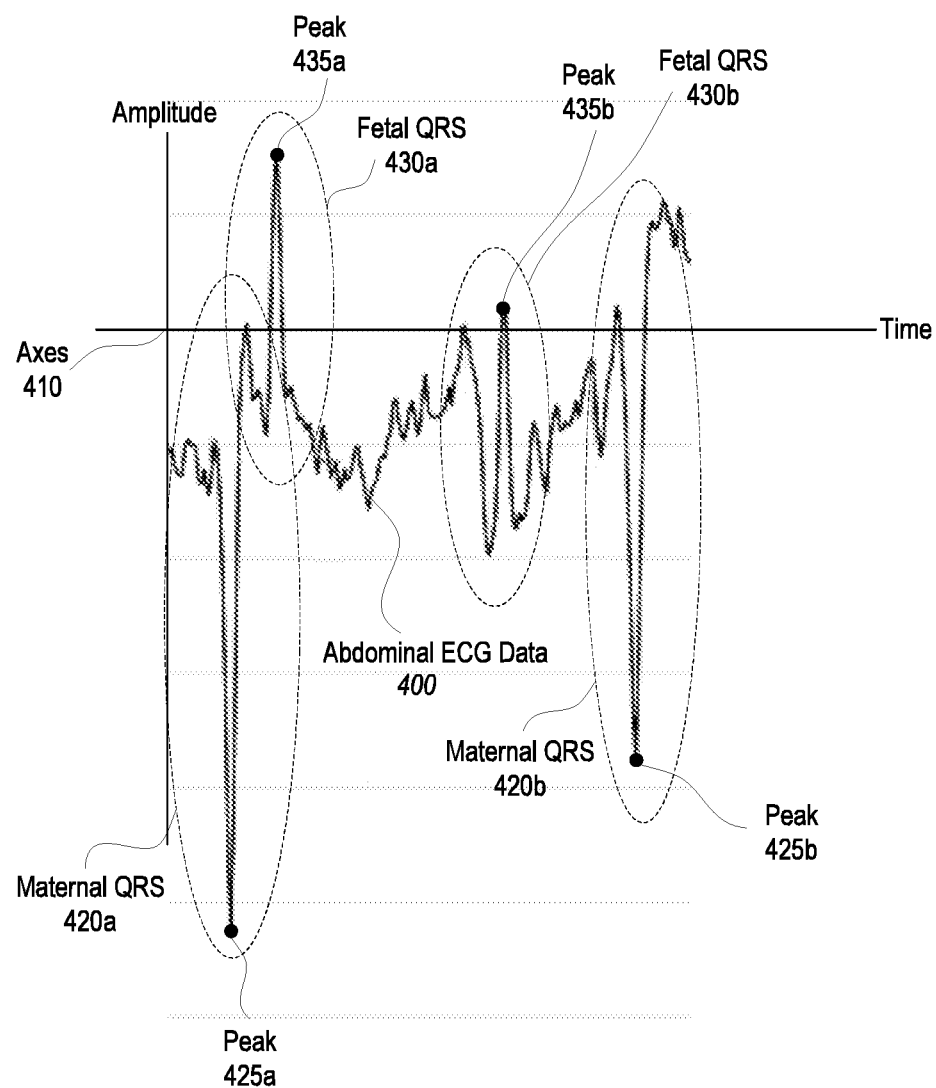
FIG. 4 illustrates an exemplary QRS complex of an ECG measurement.

FIG. 4 illustrates an exemplary QRS complex 400 of an ECG measurement. While a single QRS complex is shown in FIG. 4, it will be appreciated that, in some embodiments, ECG measurements include multiple QRS complexes.

The QRS complex is plotted on a set of axes 410, with the vertical axis being amplitude and the horizontal axis being time. Peaks 425a, 425b, 435a, and 435b are the maxima and minima of QRS complex 400. The QRS complex 400 is representative or typical of QRS complexes in an ECG measurement, such as a maternal QRS complex 420(a, b) or fetal QRS complex 430(a, b) that appears in ECG measurements of maternal or fetal heart rates. Those skilled in the art will appreciate the various differences between fetal and maternal QRS complexes, such as amplitude, periodicity, frequency content, and other parameters.

Figure 5:
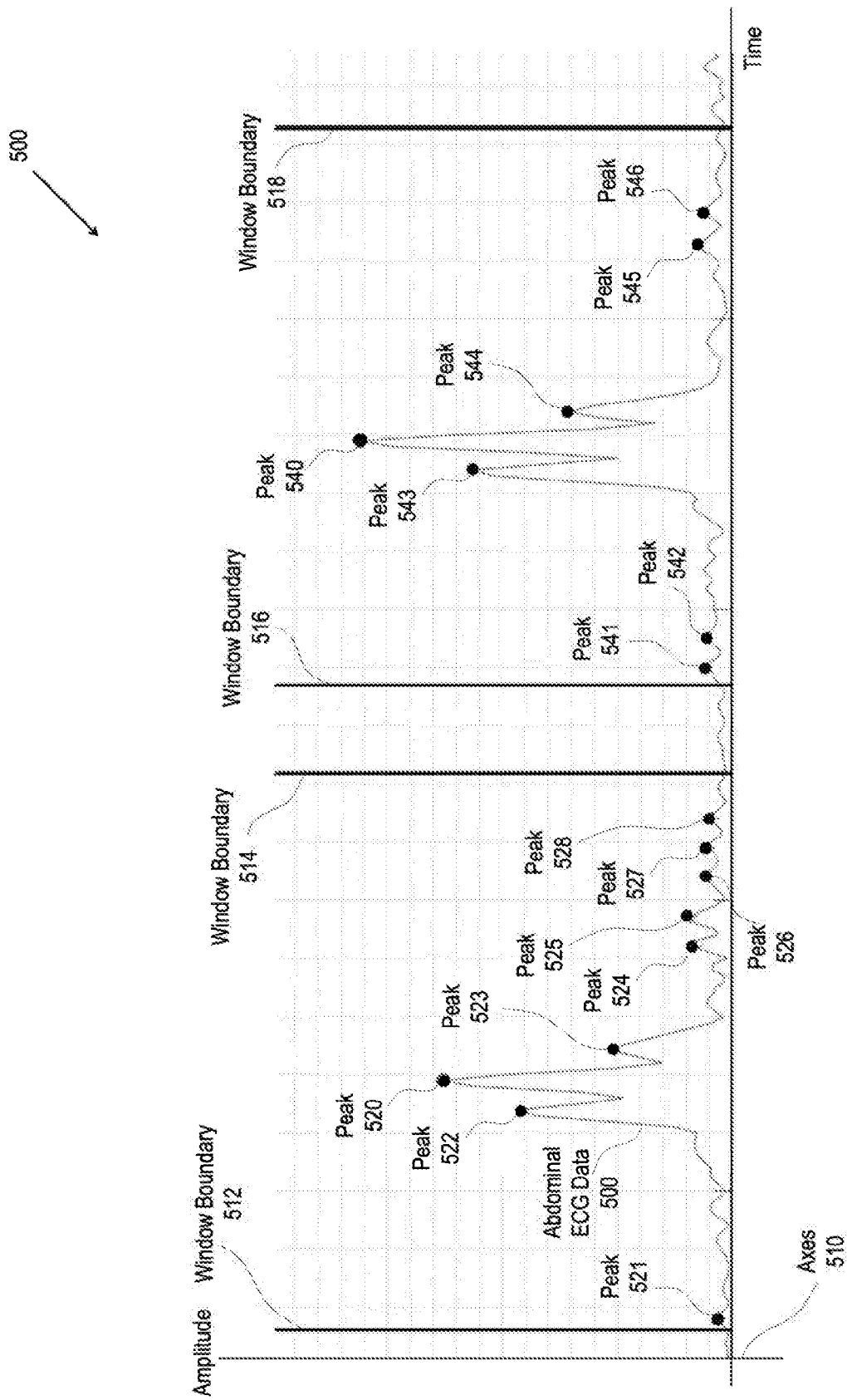
FIG. 5 illustrates an exemplary absolute value QRS complex of an ECG measurement.

FIG. 5 illustrates an exemplary absolute value QRS complex 500 of an ECG measurement. In some embodiments, the absolute value of ECG measurements is taken to aid in processing. In some embodiments, taking the absolute value of the ECG measurements has the advantage of simplifying processing or analysis of the ECG measurements. In some such embodiments, this simplification is the result of the relaxing or removal of constraints on the processing or analysis.

Absolute value QRS complex 500 is plotted on a set of axes 510, with the vertical axis being amplitude and the horizontal axis being time. Peaks 520, 521, 522, 523, 524, 525, 527, 528, 540, 541, 542, 543, 544, 545, and 546 are the maxima of absolute value QRS complex 500.

Boundaries 512, 514, and 516 indicate the edge of time steps or windows. In FIG. 5, the time between boundaries 512 and 514 indicate a first window or time step and the time between boundaries 514 and 516 indicate a second window or time step. Each time step is intended to capture or mark out a single heartbeat from a single person. For example, the window between boundaries 512 and 514 includes a single beat of the absolute value QRS complex 500.

In embodiments when measuring combined ECGs of a mother and fetus, there can be more than one heartbeat in a window, as both the mother and fetus have heartbeats in the same signal. Further, a different window size may be used for the mother than the fetus because the heartbeats can have different periods.

In FIG. 5, two beats are depicted, the first in the window between boundaries 512 and 514 and the second in the window between the boundaries 514 and 516. For the first beat, peak 520 is representative of the R peak, peak 522 is representative of the Q peak, and peak 523 is representative of the S peak. For the second beat, peak 540 is representative of the R peak, peak 543 is representative of the Q peak, and peak 544 is representative of the S peak.

The absolute value QRS complex 500 is representative of QRS complexes in an ECG measurement after the absolute value of the ECG measurement has been taken. For example, the absolute value QRS complex 500 could be the absolute value of a maternal or fetal QRS complex that appears in ECG measurements of maternal or fetal heart rates. Those skilled in the art will appreciate the various differences between fetal and maternal QRS complexes, such as amplitude, periodicity, frequency content, and other parameters.

Figure 6:
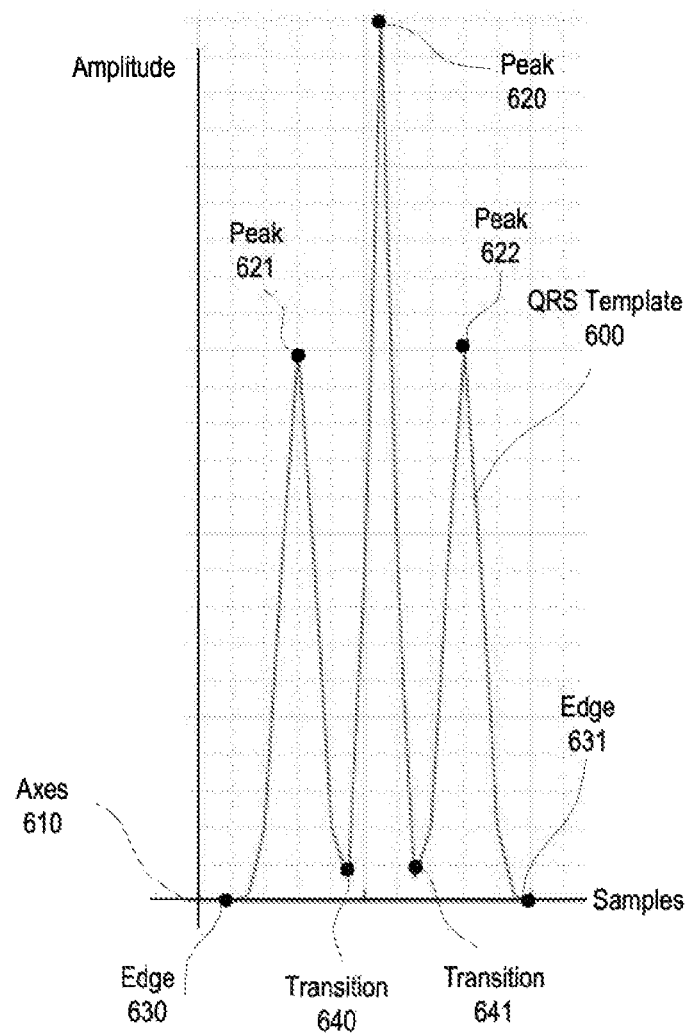
FIG. 6 shows an exemplary QRS template.

FIG. 6 shows an exemplary QRS template 600 with a first and second edge 630, 631 and a first and second transition 640, 641. This embodiment of a QRS template is the absolute value of the QRS complex. Peak 620 is representative of the R peak, peak 621 is representative of the Q peak, and peak 622 is representative of the S peak. QRS complex 600 is plotted on a set of axes 610, with the vertical axis being amplitude and the horizontal axis being time.

In some embodiments, QRS template 600 is a maternal QRS template. In such embodiments, QRS template 600 has parameters or characteristics more appropriate for a maternal QRS complex. For example, the amplitude of the peaks 620, 621, and 622 will be set to values that correspond to a maternal QRS complex. In some embodiments, a QRS template 600 that is a maternal QRS template will be adjusted or modified based on known information about the heart rate and QRS complex of a specific patient who is to be monitored.

In some embodiments, QRS template 600 is a fetal QRS template. In such embodiments, QRS template 600 has parameters or characteristics more appropriate for a fetal QRS complex. For example, the amplitude of the peaks 620, 621, and 622 will be set to values that correspond to a fetal QRS complex.

Figure 7:
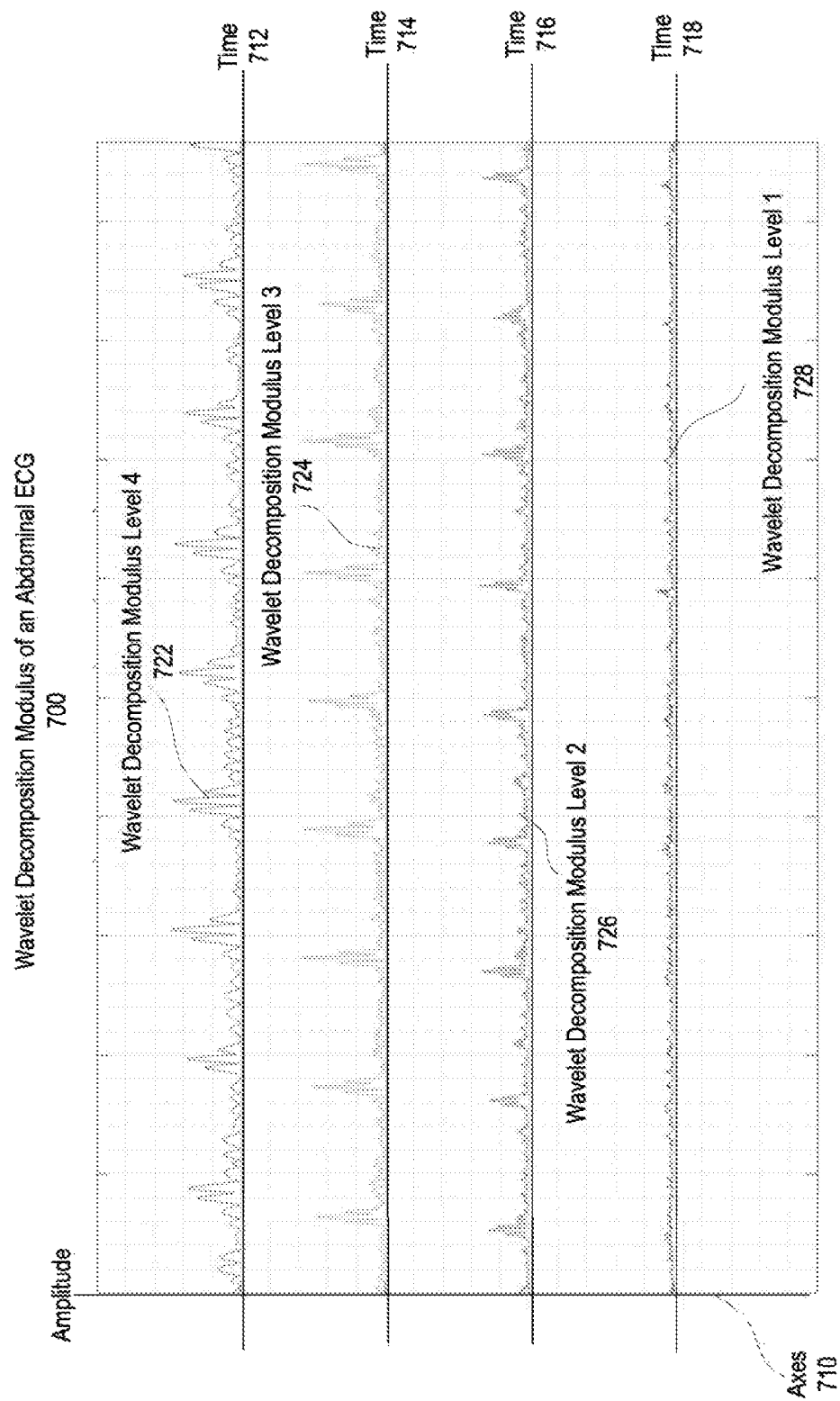
FIG. 7 depicts an exemplary absolute value of a noisy fetal QRS complex.

FIG. 7 depicts the absolute value of a noisy fetal QRS complex 700. The graph of FIG. 7 depicts the wavelet decomposition modulus at levels 1-4 (shown as 722, 724, 726, and 728). One will appreciate that the wavelet decomposition modulus at levels 1-4 (722, 724, 726, and 728) are shown on axes 710 that comprise a single amplitude axis that is relative to each individual bisecting time axis 712, 714, 716, 718. As is apparent from the presented data, there is significant noise within the ECG signal. The inclusion of the maternal QRS complex on top of the fetal QRS complex presents significant difficulty for isolating the fetal heart rate information from the noisy signal.

Attention will now be turned to several aspects of the block diagram of FIG. 1. For specific blocks that perform complex functions, FIGS. 8-11 provide additional detail on those functions.

Figure 8:
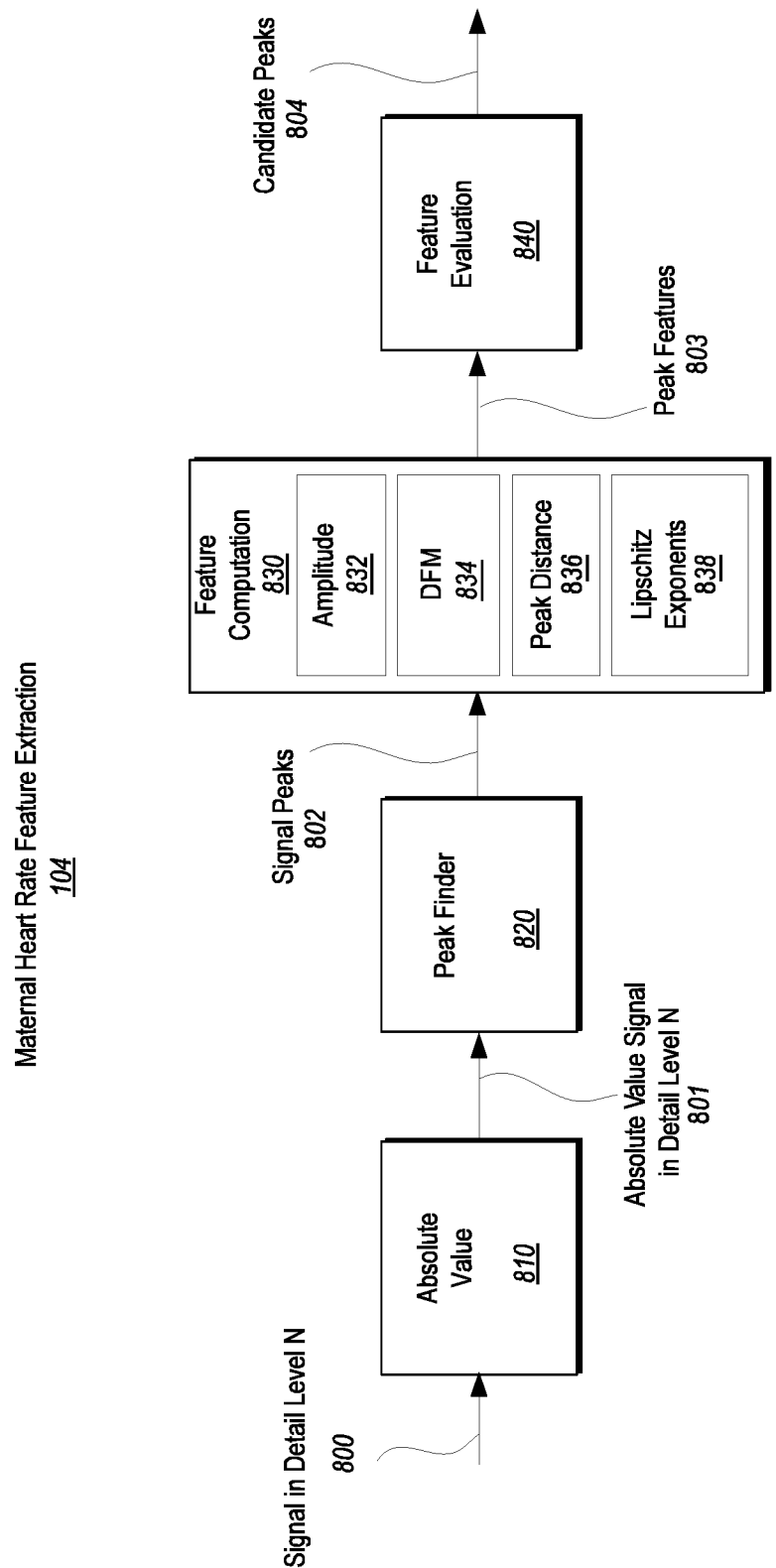
FIG. 8 illustrates greater detail on an embodiment of a maternal heart rate feature extraction.

FIG. 8 illustrates greater detail on maternal heart rate feature extraction 104. As described above, maternal heart rate feature extraction 104 takes as an input signal in detail level N 800, which is a signal or measurement in the Nth detail level of a wavelet transform of the signal or measurement. The signal is processed or analyzed to identify a number of candidate peaks 804 as an output. Candidate peaks 804 are maxima of the signal in detail level N 800 which are candidates for corresponding to an actual R-peak of a QRS complex in an ECG measurement.

In some embodiments, detail level N is detail level three of a four-level wavelet transform of the signal or measurement being analyzed. In some embodiments, detail level N is a detail level that includes at least 12.5 Hz to 25 Hz. In some embodiments, detail level N is a detail level that includes at least 5 Hz to 35 Hz.

To identify the candidate peaks 804, maternal heart rate feature extraction 104 first takes signal in detail level N 800 and finds the absolute value of the signal using absolute value 810. The output is absolute value signal in detail level N 801.

Next the signal peaks 802 of absolute value signal in detail level N 801 are found using peak finder 820. In some embodiments, peak finder 820 finds the peaks by sequentially processing the samples of absolute value signal in detail level N 801. Those skilled in the art will appreciate the various peak finding techniques available and which can be used to find the peaks of absolute value signal in detail level N 801. In some embodiments, signal peaks 802 are referred to as wavelet transform modulus maxima(e) (wtmm).

As an example, consider FIG. 5, depicting absolute value QRS complex 500. In the window between boundaries 512 and 514, peaks 520, 521, 522, 523, 524, 525, 526, 527, and 528 exist. Depending on the peak finding algorithm or technique used, peak finder 820 identifies one or more of peaks 520, 521, 522, 523, 524, 525, 526, 527, and 528 as the signal peaks 802 of absolute value QRS complex 500. In some embodiments, peak finder 820 identifies at least two of peaks 520, 521, 522, 523, 524, 525, 526, 527, and 528 as signal peaks 802. In some embodiments, peak finder 820 identifies all of peaks 520, 521, 522, 523, 524, 525, 526, 527, and 528 as signal peaks 802.

Signal peaks 802 are then processed by feature computation 830 to identify peak features 803. Feature computation 830 includes finding, processing, calculating, determining, identifying, or otherwise obtaining one or more parameters. Example parameters include of a signal peak of the signal peaks 802 include amplitude of a peak, found by amplitude 832, distance-from-mean score, found by DFM 834, peak-to-peak distance, found by peak distance 836, and Lipschitz Exponents, found by Lipschitz Exponents 838.

In at least one embodiment, Amplitude 832 is provided for each identified peak (e.g., peaks 520, 521, 522, 523, 524, 525, 526, 527, and 528 from FIG. 5). In at least one additional or alternative embodiment, Amplitude 832 is calculated using conventional means known in the art. The Amplitude 832 may be designate as $y_{mhr}(n)$ of the wtmm.

In at least one embodiment, DFM 834 is computed as follows:

$$y_{maternal\text{-}dfm\text{-}score} = \frac{abs(y(n)) - \mu_{mhr}(n)}{\mu_{mhr}(n)} \quad \text{Equation 1}$$

In Equation 1, n is the sample index of wtmm and $\mu_{mhr}(n)$ is the value of the $n^{th}$ sample of the running mean $\mu_{mhr}$. The mean signal $\mu_{mhr}$ is obtained by filtering the Detail Level 3 signal with a first-order IIR filter. y(n) is the amplitude of the $n^{th}$ sample of the Level 3 Signal.

In at least one embodiment, Peak Distance 836 is calculated based upon the number of samples between consecutive wtmm.

In at least one embodiment, the Lipschitz Exponents 838 is used to characterize signal singularities. For example, the Lipschitz Exponent may be used to detect QRS complexes which appear as transient abruptions (i.e., signal singularities) in the ECG baseline. The computation of the Lipschitz exponent requires the identification of corresponding wtmm in the neighboring levels. The neighboring scales for Detail Level 3 are Levels 1, 2, and 4. Let $y_{l1}(n)$, $y_{l2}(n)$, and $y_{l4}(n)$ denote the amplitudes of the wtmm in Levels 1, 2, and 4 that correspond to the wtmm y(n) of Level 3. The decay $\alpha_i$ of y(n) from Level 3 to Level i is expressed using the modified regularity exponent provided below:

$$\alpha_i = \log_2 y_3 - \log_2 y_i \quad \text{Equation 2}$$

Based on the modified regularity exponents $a_1$, the Lipschitz Exponent LE(y(n)) for the m-QRS candidate wtmm y(n), is calculated using the below equation 3.

$$LE(y(n)) = \Sigma_{i=1}^{3} \alpha_i \quad \text{Equation 3}$$

In some embodiments, one or more of amplitude 832, DFM 834, peak distance 836, or Lipschitz Exponents 838 are used in feature computation 830. In some embodiments, all of amplitude 832, DFM 834, peak distance 836, and Lipschitz Exponents 838 are used in feature computation 830.

Peak features 803 contains whichever parameters are found in feature computation 830. For example, in embodiments where Amplitude 832, DFM 834, peak distance 836, or Lipschitz Exponents 838 are used in Feature Computation 830, for each signal peak of signal peaks 802, peak features 803 will include that signal peak, the amplitude of that signal peak found by amplitude 832, the distance from mean score of that signal peak found by DFM 834, a distance between that signal peak and at least one other signal peak that is closest to that signal peak on either side found by peak distance 836, and a Lipschitz Exponent for that signal peak found by Lipschitz Exponent 838.

In at least one embodiment, feature evaluation 840 uses each of the above four features 832, 834, 836, 838 to compare against a threshold. Only those candidate wtmms that satisfy all four conditions are retained and passed to the next stage (Stage 3). Hereafter, these candidates are referred to as candidate peaks 804 (also referred to as m-QRS candidates) for the location of R-peak.

Figure 9:
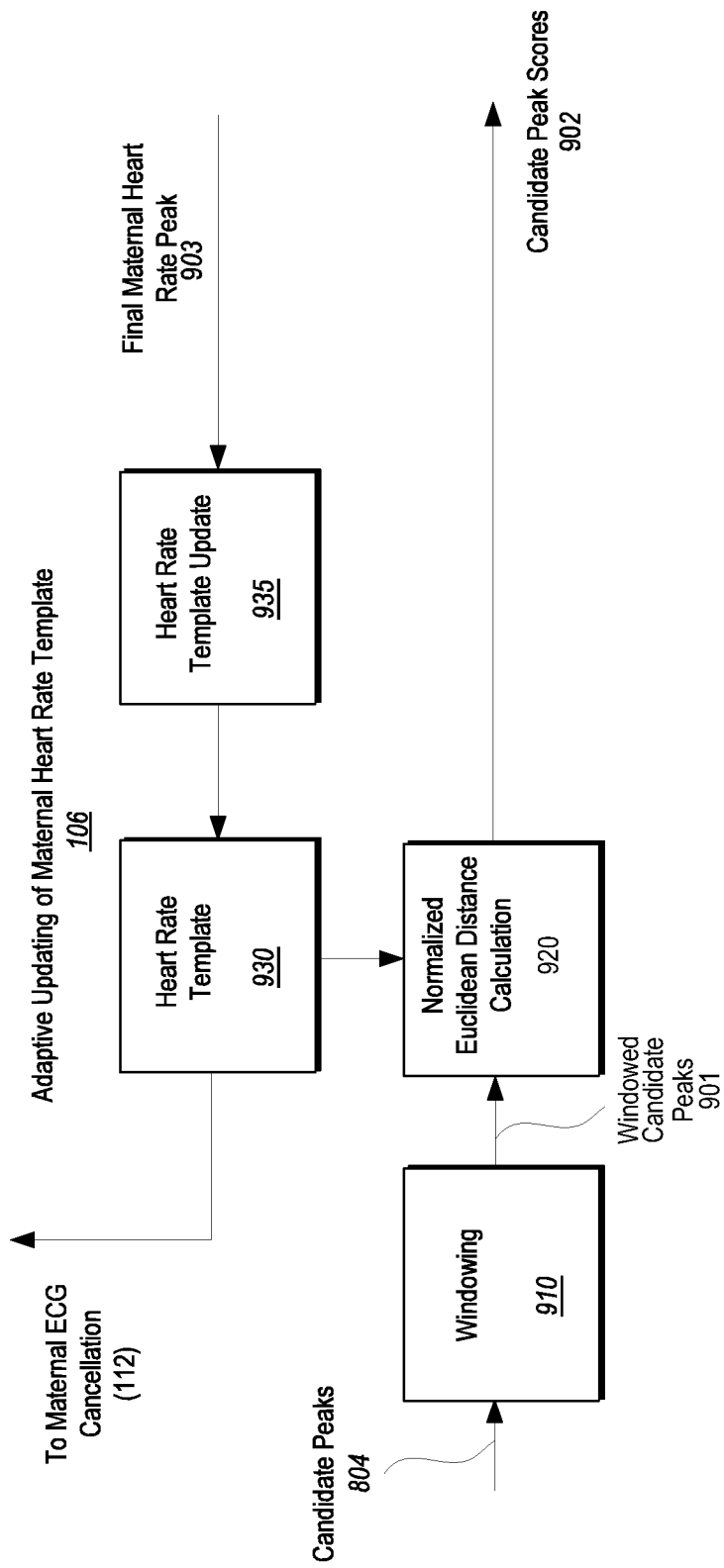
FIG. 9 illustrates greater detail on an embodiment of an adaptive updating of maternal heart rate template.

FIG. 9 illustrates greater detail on adaptive updating of maternal heart rate template 106. In this stage, a template of the shape of the maternal QRS waveform is generated. The shape of the m-QRS waveform varies from woman to woman and it also changes through the course of the pregnancy.

Within the adaptive updating of maternal heart rate template 106, the candidate peaks 804 are provided to the windowing 910. A window, $h_{N,i}(n)$ of length N samples centered around each of candidate locations i, of the maternal R-peak is taken (shown as Windowed Candidate Peaks 901). The Windowed Candidate Peaks 901 are then compared to a maternal QRS Heart Rate Template 930, $g_N$, using a novel distance metric, herein referred to as normalized Euclidean distance. It is also alternatively referred to as the template matching score $t_{score}$ or the normalized Euclidean-Distance score. The location of these m-QRS candidates and their corresponding template-matching scores are then fed to the Dynamic Maternal Heart Rate Search 108, also referred to here as "dynamic programming based Probabilistic m-QRS/MHR Search Scheme."

The Normalized Euclid Distance Calculation 920 is calculated as outlined below:

Area under the window, Equation 4

$$hmaternal_{area} = \sum_{k=-\frac{N}{2}+1}^{\frac{N}{2}} (h_{N,i}(k) - h_{N,i}(k-1))$$

Area under the template, Equation 5

$$gmaternal_{area} = \sum_{k=-\frac{N}{2}}^{\frac{N}{2}} (g_N(k) - g_N(k-1))$$

Gain of the Template, $Tmaternal_{gain} = \dfrac{hmaternal_{area}}{gmaternal_{area}}$ Equation 6

$$tf_{fetal\text{-}score} = f_{mat\text{-}norm\text{-}euclid\text{-}dist}((h_{N,i}, g_N)) = \quad \text{Equation 7}$$

$$\sqrt{\sum_{k=-\frac{N}{2}}^{\frac{N}{2}} \left( \frac{hmaternal_{N,i}(k) - gmaternal_N(k))^2}{Tmaternal_{gain}} \right)}$$

Equations 4-7 are used to compute the maternal template matching score, $tmaternal_{score}$. Once the final maternal R-peak location has been identified, the Final Maternal Heart Rate Peak 903 is fed into a Heart Rate Template Update step 935 and the Heart Rate Template, $g_N$, is then adaptively adjusted as shown below in Equation 8.

$$g_N(m+1) = \alpha_g * h_{N,final\text{-}R\text{-}peak} + (1-\alpha_g) * g_N(m) \quad \text{Equation 8}$$

In at least one embodiment, a universal initial template $g_{N,0}$ is used to seed the maternal template estimation algorithm. Similarly, templates can be generated for the corresponding components of the maternal QRS complex in the neighboring levels (Levels 1, 2, & 4). The output of this stage is a set of candidate maternal R-peak locations ($y_i$) and their corresponding template matching scores $t_{sore,y_i}$.

Returning to the flow chart of FIG. 1, Dynamic Maternal Heart Rate Search 108 is used to select the candidate m-QRS location that maximizes a probabilistic cost function. In at least one embodiment, the Dynamic Maternal Heart Rate Search 108 is referred to as a "dynamic programming based Probabilistic m-QRS/MHR Search Scheme." For example, let m denote the number of maternal R-peaks that has been detected by the algorithm so far. Let $tf_{maternail\_score}$ denote the final scores for the $N_m$ m-QRS candidates. Let y(m−1), denote the set of m-QRS candidates detected at the (m−1)$^{th}$ pass through a Probabilistic m-QRS/MHR Search scheme. The cost function for the i$^{th}$ m-QRS candidate is then given by Equation 9 below:

$$P(tf_{score,i}(m), tf_{score,k}(m-1), y_i(m), y_k(m-1)) = tf_{score,i}(m) * \quad \text{Equation 9}$$

$$tf_{score,k}(m-1) * e^{-\frac{1}{2 * \sigma_{mhr}^2(m-1)} \left( \frac{60 * \beta}{((y_i(m) - y_k(m-1))} - \mu_{mhr}(m-1) \right)^2}$$

$$y_{final,mQRS}(m) = \underset{y_i(m)}{\operatorname{argmax}} P_{total}(y_i(m-1)) *$$

$$P(tf_{score,i}(m), tf_{score,k}(m-1), y_i(m), y_k(m-1))$$

Following the Dynamic Maternal Heart Rate Search 108, the Maternal Heart Rate Estimation 110 is performed to identify the Final Maternal Heart Rate. In at least one embodiment, the Final Maternal Heart Rate is estimated as provided below by Equation 10.

$$z_{mhr}(m) = \frac{60 * Fs}{(y_i(m) - y_k(m-1))} \quad \text{Equation 10}$$

Based on $z_{mhr}(m)$, $\mu_{mhr}$ and $\sigma_{mhr}$ are updated as follows, $$\mu_{mhr}(m) = \alpha_\mu * z_{mhr}(m) + (1-\alpha_\mu) * \mu_{mhr}(m-1) \quad \text{Equation 11}$$

$$\sigma_{mhr}(m) = \alpha_\sigma * z_{mhr}(m) + (1-\alpha_\sigma) * \sigma_{mhr}(m-1) \quad \text{Equation 12}$$

Once the Maternal Heart Rate Estimation 110 is performed, the Maternal ECG Cancellation 112 removes the Maternal ECG signal from the QRS complex 400 (shown in FIG. 4). As an example method for Maternal ECG Cancellation 112, let $x_{wecg}(t, l)$ denote the multiresolution wavelet decomposition of the abdominal ECG signal $x_{aecg}(t)$ at level l. Furthermore, let $g_{N,l}(m)$ denote the template of the maternal QRS complex for the level l. Once the final m-QRS location ($y_{final,mQRS}(m)$) has been identified (shown in Equation 9), the multiresolution wavelet decomposition of the fetal ECG signal is calculated as follows:

$$x_{fecg}(t,l) = x_{wecg}(t,l) - g_{N,l}(m)$$

$$\forall (y_{final,mQRS}(m) - N_1) < t < y_{final,mQRS}(m) + N_2) \quad \text{Equation 13}$$

In Equation 13, $N_1$ and $N_2$ are the number of samples around the final maternal R-peak.

Figure 10:
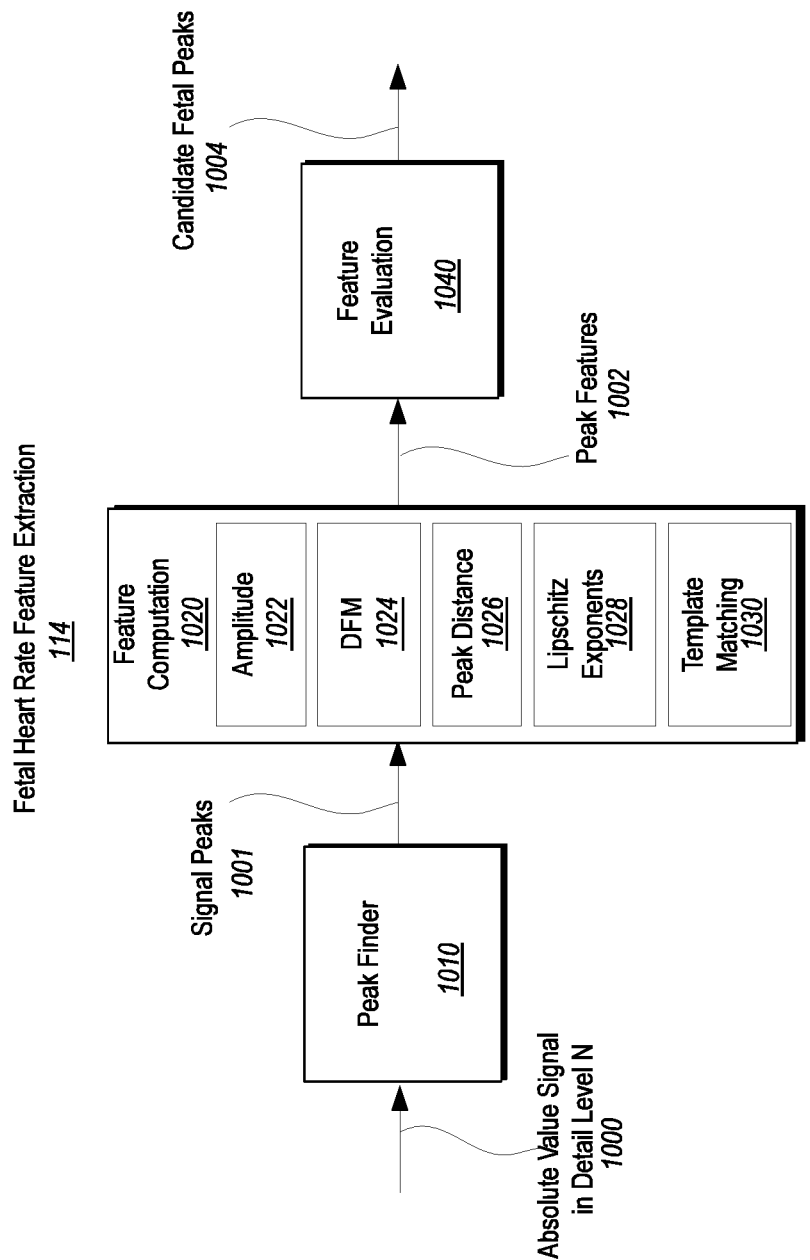
FIG. 10 illustrates greater detail on an embodiment of a Fetal Heart Rate Extraction step.

After the Maternal ECG Cancellation 112, the system transitions from the Maternal Side 140 of the Abdominal Electrocardiogram Processing System Block Diagram Overview of FIG. 1 and into the Fetal Side 150. In at least one embodiment, the Fetal Heart Rate Feature Extraction 114 depicted in FIG. 10 is then performed. As indicated above, the signal received by the Fetal Heart Rate Feature Extraction 104 comprise the Absolute Value Signal in Detail Level N 1000, which is the output of the Maternal ECG Cancellation 112.

In the Fetal Heart Rate Feature Extraction 104 stage, the Peak Finder 1010 sequentially processes the samples of the Wavelet-domain fECG signal (fetal ECG) to identify the Signal Peaks 1001 (i.e., local modulus maxima); these Signal Peaks 1001 are also referred to herein as "fetal-wtmm." Once a fetal-wtmm has been identified, the Feature Computation 1020 identifies various features. Examples of the computed features include amplitude of a peak (calculated in stage Amplitude 1022), distance from mean score (calculated in stage DFM 1024), distance between peaks (calculated in stage Peak Distance 1026), Lipschitz Exponents (calculated in stage Lipschitz Exponents 1028), and template matching (calculated in stage Template Matching 1030).

In at least one embodiment, the Amplitude 1022, also referred to herein as $y_{fetal}(n)$, is provided for each identified peak. In at least one additional or alternative embodiment, the Amplitude 1022 is calculated using conventional means known in the art.

In at least one embodiment, DFM 1024 (also referred to herein as "fetal-DFM score") is computed as follows:

$$y_{fetal-dfm-score} = \frac{\text{abs}(x_{fecg}(n)) - \mu_{fecg}(n)}{\mu_{fecg}(n)} \quad \text{Equation 14}$$

In Equation 14, n is the sample index of the fetal-wtmm and $\mu_{fecg}(n)$ is the value of the nth sample of the running mean of the Wavelet-domain fECG signal.

Additionally, in at least one embodiment, the Peak Distance 1026 (also referred to herein as $N_{minmax}$) is calculated based upon the number of samples, between consecutive fetal-wtmm.

In at least one embodiment, the Lipschitz Exponents 1028 are used to characterize signal singularities. The Lipschitz Exponents 1028 are used to detect QRS complexes which appear as transient abruptions (i.e., signal singularities) in the fECG baseline. The computation of the Lipschitz Exponents 1028 requires the identification of corresponding fetal-wtmm in the neighboring levels. The neighboring scales for Detail Level 2 are Levels 1 and 3. For example, let $y_{fetal-l1}(n)$ and $y_{fetal-l3}(n)$ denote the amplitudes of the fetal-wtmm in Levels 1 and 3 that correspond to the fetal-wtmm $y_{fetal}(n)$ of Level 2. The decay $\alpha_i$ of y(n) from Level 2 to Level i is expressed using the modified fetal regularity exponent as indicated in Equation 15 below:

$$\alpha_{fetal-i} = \log_2 y_{fetal-l3} - \log_2 y_{fetal-i} \quad \text{Equation 15}$$

Based on the modified regularity exponents $a_i$, the Lipschitz Exponent $LE_{fetal}(y_{fetal}(n))$ for the fetal QRS (i.e., "f-QRS") candidate fetal-wtmm $y_{fetal}(n)$, is calculated as follows, $$LE(y_{fetal}(n)) = \Sigma_{i=1}^2 \alpha_{fetal-i} \quad \text{Equation 16}$$

In the Template Matching 1030 stage, a template of the shape of the fetal QRS waveform is generated and compared against a reference. The shape of the f-QRS waveform varies for each fetus woman-to-woman and it also changes through the course of the pregnancy. A window, $hfetal_{N,i}(n)$ of length N samples centered around each of candidate locations i, of the fetal R-peak is taken and then compared to a fetal QRS template, $g_N$ using the novel Euclidean Distance Equation disclosed above. It is also alternatively referred to as the fetal template matching score $t_{fetal-score}$. This score is referred to as the normalized fetal Euclidean-Distance score and is disclosed above in Equation 4. One of skill in the art will appreciate that Equation 4 is recited with respect to maternal ECG measurements, but the modification for fetal measurements are readily apparent. The location of these Candidate Fetal Peaks 1004, also referred to as Fetal R-peak (i.e., f-QRS), and their corresponding template-matching scores are then fed to the Dynamic Fetal Heart Rate Search 116, also referred to herein as "dynamic programming based Probabilistic m-QRS/MHR Search Scheme."

Figure 11:
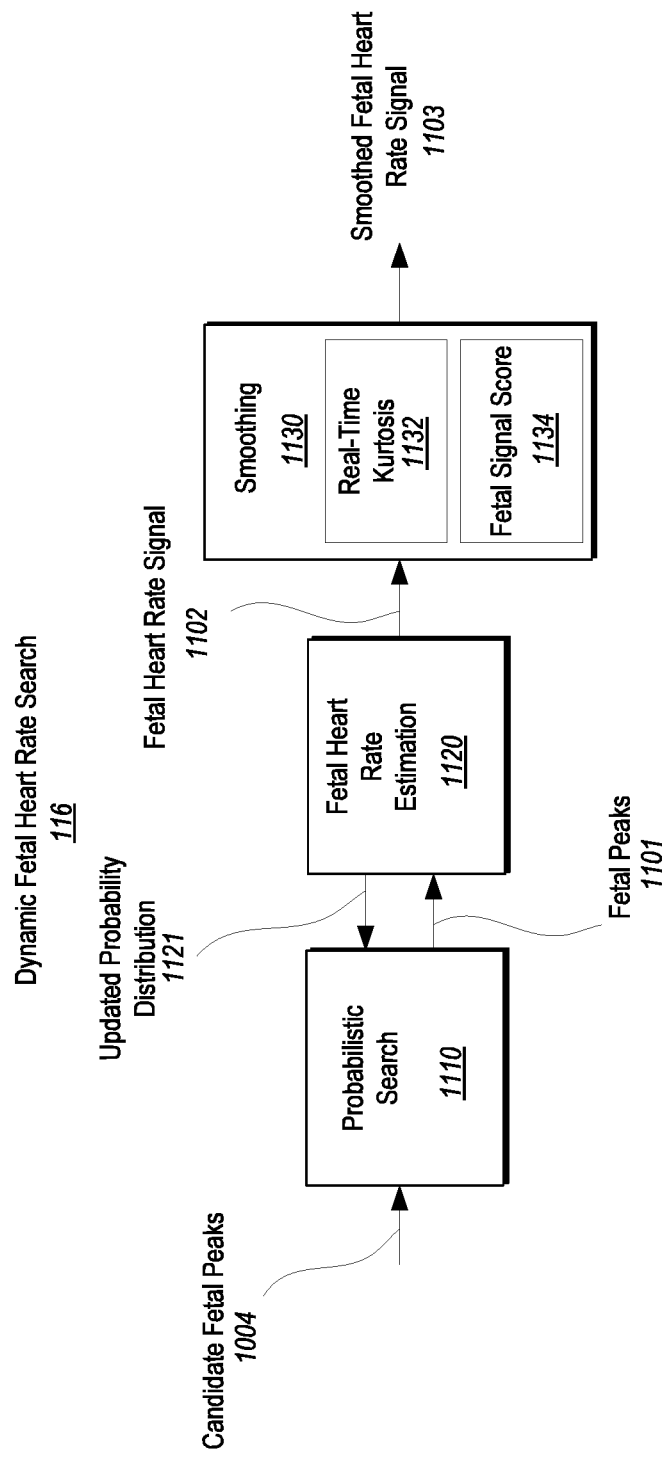
FIG. 11 illustrates greater detail on an embodiment of a Dynamic Fetal Heart Rate Search step.

FIG. 11 depicts the Dynamic Fetal Heart Rate Search 116 in detail. As depicted, the Candidate Fetal Peaks 1004 are received by the Probabilistic Search 1110. The Probabilistic Search 1110 is used to select the candidate f-QRS location that maximizes a probabilistic cost function. For example, let m denote the number of fetal R-peaks that have been detected by the algorithm. Let $tf_{fetal-score}$ denote the final scores for the $N_m$ f-QRS candidates. Let $y_{fetal}(m-1)$, denote the set of f-QRS candidates detected at the $(m-1)^{th}$ pass through Probabilistic f-QRS/FHR Search scheme (i.e., the Probabilistic Search 1110). The cost function for the $i^{th}$ f-QRS candidate is then given by the following Equation 17.

$$P(tf_{fetal-score,i}(m), tf_{fetal-score,k}(m-1), y_i(m), y_k(m-1)) = \quad \text{Equation 17}$$

$$tf_{fetal-score,i}(m) * tf_{fetal-score,k}(m-1) *$$

$$e^{-\frac{1}{2*\sigma_{fhr}^2(m-1)}\left(\frac{60*\beta}{((y_i(m)-y_k(m-1))} - \mu_{fhr}(m-1)\right)^2}$$

$$y_{final,fQRS}(m) = \underset{y_{fetal-i}(m)}{\text{argmax}} \; P_{total}(y_{fetal-i}(m-1)) *$$

$$P(tf_{fetal-score,i}(m), tf_{fetal-score,k}(m-1), y_i(m), y_k(m-1))$$

Following the Dynamic Fetal Heart Rate Search 116, the Fetal Heart Rate Estimation 1120 is performed. In at least one embodiment, the Fetal Heart Rate Signal 1102 is estimated as provided below by Equation 18.

$$z_{fhr}(m) = \frac{60 * Fs}{(y_{fetal-i}(m) - y_{fetal-k}(m-1))} \quad \text{Equation 18}$$

Based on $z_{fhr}(m)$, $\mu_{fhr}$ and $\sigma_{fhr}$ are updated as follows, $$\mu_{fhr}(n) = \alpha_\mu * z_{fhr}(m) + (1-\alpha_\mu) * \mu_{fhr}(m-1) \quad \text{Equation 19}$$

$$\sigma_{fhr}(m) = \alpha_\sigma * z_{fhr}(m) + (1-\alpha_\sigma) * \sigma_{fhr}(m-1) \quad \text{Equation 20}$$

The Updated Probability Distribution 1121 is then provided to Probabilistic Search 1110 through feedback.

In at least one embodiment Smoothing 1130 is applied to the Fetal Heart Rate Signal 1102 (i.e., $z_{fhr}(m)$) to obtain a Smoothed Fetal Heart Rate Signal 1103 (i.e., $z_{smoothed-fhr}(m)$). Additionally, in at least one embodiment, the Smoothing 1130 may comprise a Real-time Kurtosis 1132 and a Fetal Signal Score 1134 for estimating the quality of detected of fetal QRS beats.

In at least one embodiment, the Real-time Kurtosis 1132 comprises a Real-time Kurtosis Score for a given fetal beat. The Real-time Kurtosis Score is calculated as follows:

$$kurt_{fetal}(n) = \quad \text{Equation 21}$$
$$\delta_3 * \left(\frac{y_{fetal}(n) - \mu_{fetal}(n)}{\sigma_{fetal}}\right)^4 + (1-\delta_3) * kurt_{fetal}(n-1)$$
$$\sigma_{fetal}(n) = \delta_2 * (y_{fetal}(n) - \mu_{fetal}(n))^2 + (1-\delta_2) * \sigma_{fetal}(n-1)$$
$$\mu_{fetal}(n) = \delta_1 * x_{aecg}(n) + (1-\delta_1) * \mu_{fetal}(n-1)$$

Additionally, in at least one embodiment, the Fetal Signal Score 1134 is calculated at indicated below by Equation 22.

$$fQRS_{beatscore}(n, k) = \frac{1}{N_c} * \sum_{i=1}^{N_c} 20 * \log 10\left(\frac{tf_{score,k}(n)}{tf_{score,i}(n)}\right) \quad \text{Equation 22}$$

In Equation 22, $N_c$ is the number of fQRS candidates at timestep n.

The Dynamic Fetal Heart Rate Search 116 identifies the final fetal peaks with kurtosis scores in a first predetermined range and signal scores in a second predetermined range and outputs the Smoothed Fetal Heart Rate Signal. In at least one embodiment, the first predetermined range of kurtosis scores and/or the second predetermined range of signal scores may be dynamically determined or may comprise static thresholds. In at least one additional or alternative embodiment, the Smoothed Fetal Heart Rate Signal 1103 can be displayed to user on a user interface, used to identify abnormalities in fetal heart rate, used to track and log fetal health, and/or used for any number of different medical and health metrics.

Figure 12:
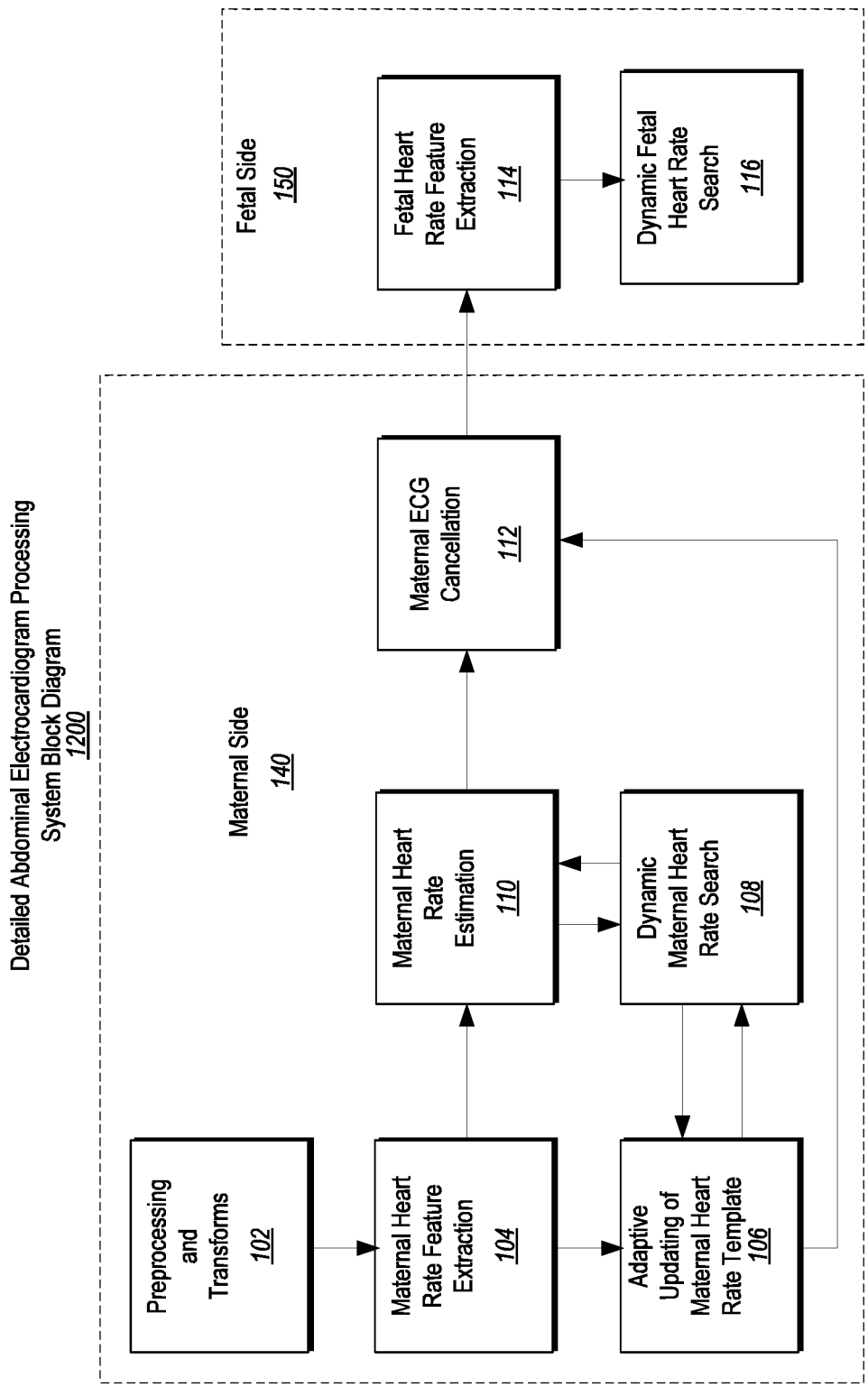
FIG. 12 illustrates another embodiment of the abdominal electrocardiogram ("ECG" or "AECG") processing system block diagram shown in FIG. 1.

FIG. 12 depicts a rearrangement of the flowchart of FIG. 1. The Detailed Abdominal Electrocardiogram Processing System Block Diagram 1200 of FIG. 12 has been drawn to depict an embodiment of the system with depicted feedback loops. One of skill in the art, in view of the above disclosure and mathematical explanations will appreciate the indicated flow of information between the different blocks 102, 104, 106, 108, 110, 112, 114, 116, 140, and 150.

One will appreciate that the present invention can also be described in terms of methods comprising one or more acts for accomplishing a particular result. For example, FIG. 13 and the corresponding text illustrate a flowchart of a sequence of acts in methods for generating an optimized coating formulation through a user interface. The acts of FIG. 13 are described below with reference to the components and modules illustrated in FIGS. 1-12.

Figure 13:
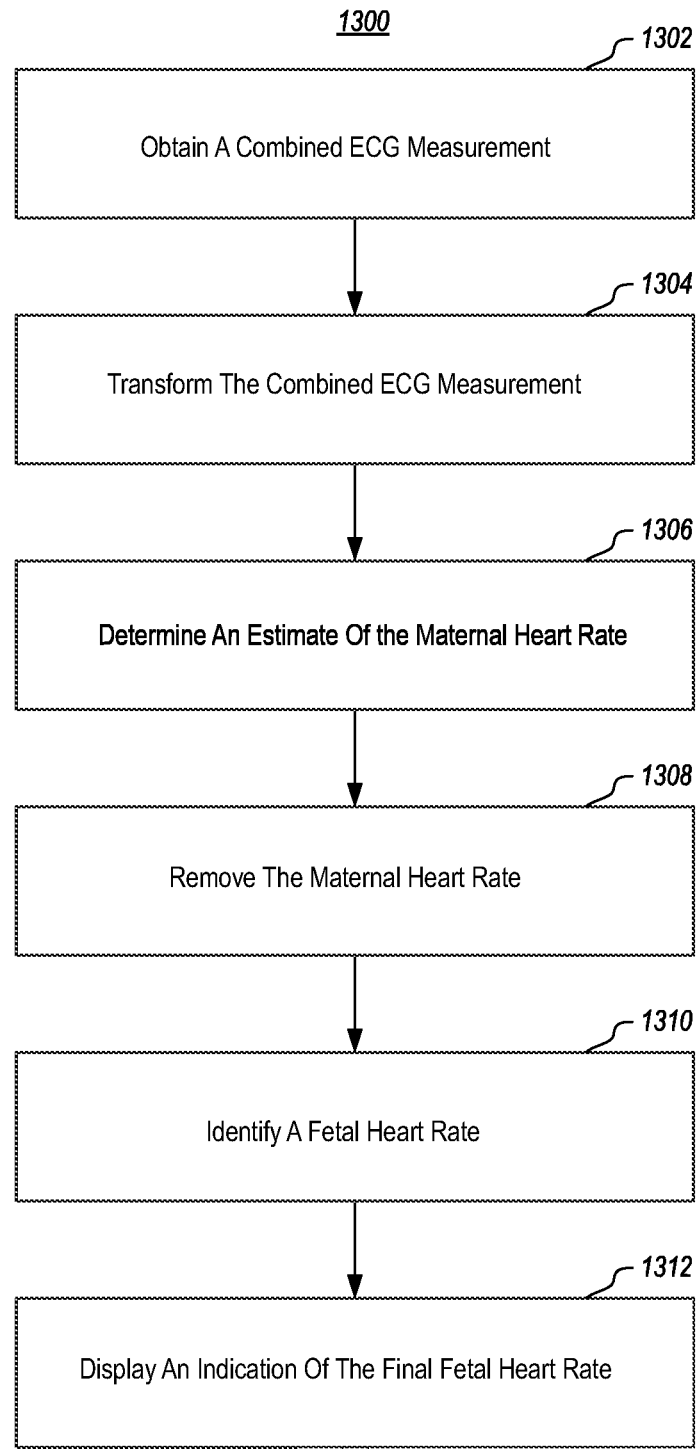
FIG. 13 illustrates a flow chart of acts in methods for generating an optimized coating formulation through a user interface.

For instance, FIG. 13 illustrates that a method 1300 for determining a fetal heart rate of a fetus in a pregnant woman includes an act 1302 of obtaining a combined ECG measurement. Act 1302 comprises obtaining a combined electrocardiogram measurement of a maternal heart rate and a fetal heart rate, wherein the combined electrocardiogram measurement is sampled at a first sample rate. For example, as depicted in FIG. 1-3, and the accompanying description, a combined ECG signal is obtained from one or more sensors 214 and processed at a processing center 212.

Method 1300 also includes an act 1304 transforming the combined ECG measurement. Act 1304 comprises transforming the combined electrocardiogram measurement into a wavelet domain to create a combined electrocardiogram measurement wavelet transform. For example, as depicted and explained with respect to the Preprocessing and Transforms step 102 of FIG. 1, the combined ECG can be transformed using a Maximal Overlap Discrete Wavelet Transform (MODWT).

Additionally, Method 1300 includes an act 1306 of determining an estimate of the maternal heart rate. Act 1306 comprises determining an estimate of the maternal heart rate from the combined electrocardiogram measurement wavelet transform, wherein determining the estimate of the maternal heart rate from the combined electrocardiogram measurement wavelet transform comprises various optional methods and systems. For example, FIGS. 8 and 9 depict and describe various optional methods and systems that can be used to determine an estimate of the maternal heart rate. Nevertheless, one will appreciate that while the method of FIGS. 8 and 9 may comprise novel and inventive features, those particular methods may not be required within the present system for determining a fetal heart rate of a fetus in a pregnant woman. For example, in at least one embodiment, the estimate of the maternal heart rate may be provided to the system through some other means.

By way of brief description of the optional methods and systems for determining an estimate of a maternal heart rate, in at least one embodiment, the Peak Finder step 820 as depicted and described with respect to FIG. 8 identifies at least one maternal wavelet transform modulus maxima in a first detail level of the combined electrocardiogram measurement wavelet transform. The Feature Computation 830 then determines one or more maternal features of the at least one maternal wavelet transform modulus maxima. The Feature Evaluation step 840 evaluates each maternal feature of the one or more maternal features against one or more predetermined criteria to identify a plurality of candidate maternal peaks.

Further, the optional methods and systems can comprise a Windowing step 910, as depicted and described with respect to FIG. 9, that obtains a set of windowed candidate maternal peaks. Each windowed candidate maternal peak in the set of windowed candidate maternal peaks is a window of a first number of samples around a candidate maternal peak of the plurality of candidate maternal peaks. A Normalized Euclidean Distance Calculation 920 can then determine a set of template matching scores for the set of windowed candidate maternal peaks. Each template matching score of the set of template matching scores may be found using a distance metric between each windowed candidate maternal peak of the set of windowed candidate maternal peaks and a maternal heart rate template.

Turning now to FIGS. 1 and 12, the optional methods and systems can comprise a Dynamic Maternal Heart Rate Search step 108 that determines a set of maternal peaks using a probabilistic likelihood search of the plurality of candidate maternal peaks that is based at least on the set of template matching scores. Using a feedback system, the Adaptive Updating of Maternal Heart Rate Template step 106 updates one or more parameters of the maternal heart rate template based at least on the set of maternal peaks to create an updated maternal heart rate template. Based upon the foregoing optional methods and systems, the Maternal Heart Rate Estimation step 110 determines an estimate of the maternal heart rate based on the set of maternal peaks and the updated maternal heart rate template.

Returning now to Method 1300 in FIG. 13, the method 1300 may also include an act 1308 of removing the maternal heart rate. Act 1308 comprises removing the maternal heart rate from the combined electrocardiogram measurement wavelet transform using the estimate of the maternal heart rate to create a compensated combined electrocardiogram measurement wavelet transform. For example, as depicted and described with respect to FIG. 1, the Maternal ECG Cancellation step 112 may comprise a process as indicated in Equation 13.

In addition, Method 1300 may include an act 1310 of identifying a fetal heart rate. Act 1310 comprises identifying a fetal heart rate from the compensated combined electrocardiogram measurement wavelet transform. wherein identifying a fetal heart comprises various optional methods and systems. For example, FIGS. 10 and 11 depict and describe various optional methods and systems that can be used to determine an estimate of the maternal heart rate. Nevertheless, one will appreciate that while the method of FIGS. 10 and 11 may comprise novel and inventive features, those particular methods may not be required within the present system for determining a fetal heart rate of a fetus in a pregnant woman. For example, in at least one embodiment, the estimate of the fetal heart rate may be provided to the system through some other means.

By way of brief description of the optional methods and systems for determining an estimate of a fetal heart rate, in at least one embodiment, Peak Finder 1010, as depicted and described with respect to FIG. 10, identifies at least one fetal wavelet transform modulus maxima in a particular detail level of a wavelet transform of the compensated combined electrocardiogram measurement wavelet transform. Feature Computation step 1020 then determines one or more fetal features 1002 of the at least one fetal wavelet transform modulus maxima. Feature Evaluation step 1040 then evaluates each fetal feature of the one or more fetal features 1002 against one or more predetermined criteria to identify a plurality of candidate fetal peaks.

Further, the optional methods and systems can comprise the Probabilistic Search step 1110, as depicted and described with respect to FIG. 11, that determines a set of preliminary fetal peaks 1101 using a probabilistic likelihood search of the plurality of candidate fetal peaks. In at least one embodiment, the Fetal Heart Rate Estimation 1120 then estimated a fetal heart rate. The Smoothing step 1130 then determines a kurtosis score 1132 and a signal score 1134 of each preliminary fetal peak in the set of preliminary fetal peaks for a given time step. The Dynamic Fetal Heart Rate Search 116 also selects a set of final fetal peaks with kurtosis scores in a first predetermined range and signal scores in a second predetermined range and outputs the Smoothed Fetal Heart Rate Signal (i.e., the final fetal peaks). Once the final fetal peaks are identified, Smoothed Fetal Heart Rate Signal 1103 can display an indication of the final fetal heart rate (Act 1312) to user on a user interface. The displayed fetal heart rate can be used to identify abnormalities in fetal heart rate, used to track and log fetal health, and/or used for any number of different medical and health metrics.

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

Embodiments of the present invention may comprise or utilize a special purpose or general-purpose computer including computer hardware, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An abdominal electrocardiogram processing computer system for determining a fetal heart rate of a fetus in a pregnant woman, the computer system comprising:
    one or more processors; and
    one or more computer-readable media having stored thereon executable instructions that when executed by the one or more processors configure the computer system to perform at least the following:
        obtain a combined electrocardiogram measurement of a maternal heart rate and a fetal heart rate, wherein the combined electrocardiogram measurement is sampled at a first sample rate;
        transform the combined electrocardiogram measurement into a wavelet domain to create a combined electrocardiogram measurement wavelet transform;
        determine an estimate of the maternal heart rate from the combined electrocardiogram measurement wavelet transform;
        remove the maternal heart rate from the combined electrocardiogram measurement wavelet transform using the estimate of the maternal heart rate to create a compensated combined electrocardiogram measurement wavelet transform;
        identify a fetal heart rate from the compensated combined electrocardiogram measurement wavelet transform, wherein identifying a fetal heart rate comprises:
            identifying at least one fetal wavelet transform modulus maxima in a particular detail level of a wavelet transform of the compensated combined electrocardiogram measurement wavelet transform,
            determining one or more fetal features of the at least one fetal wavelet transform modulus maxima,
            evaluating each fetal feature of the one or more fetal features against one or more predetermined criteria to identify a plurality of candidate fetal peaks,
            determining a set of preliminary fetal peaks using a probabilistic likelihood search of the plurality of candidate fetal peaks,
            determining a kurtosis score and a signal score of each preliminary fetal peak in the set of preliminary fetal peaks for a given time step, and
            selecting a set of final fetal peaks with kurtosis scores in a first predetermined range and signal scores in a second predetermined range; and
        display an indication of a final fetal heart rate based on the set of final fetal peaks.

2. The abdominal electrocardiogram processing computer system of claim 1, wherein the combined electrocardiogram measurement is processed entirely in a wavelet transform domain to determine the maternal heart rate and the final fetal heart rate.

3. The abdominal electrocardiogram processing computer system of claim 2, wherein the wavelet transform domain uses a Symmlets 4 wavelet as a mother wavelet.

4. The abdominal electrocardiogram processing computer system of claim 1, wherein the particular detail level is detail level two of a four level wavelet transform.

5. The abdominal electrocardiogram processing computer system of claim 1, wherein the first sample rate is between 100 Hz and 500 Hz.

6. The abdominal electrocardiogram processing computer system of claim 1, wherein the one or more fetal features of the at least one fetal wavelet transform modulus maxima comprises at least one of a peak amplitude feature, a distance-from-mean feature, a peak-to-peak distance feature, a Lipschitz exponent feature, or a template matching feature.

7. The abdominal electrocardiogram processing computer system of claim 1, wherein the one or more predetermined criteria is a threshold on each fetal feature of the one or more fetal features of the at least one fetal wavelet transform modulus maxima.

8. The abdominal electrocardiogram processing computer system of claim 1, further comprising creating an updated probability density of the fetal heart rate by updating an estimated mean value of the fetal heart rate.

9. The abdominal electrocardiogram processing computer system of claim 1, wherein determining the estimate of the maternal heart rate from the combined electrocardiogram measurement wavelet transform comprises:
    identifying at least one maternal wavelet transform modulus maxima in a first detail level of the combined electrocardiogram measurement wavelet transform;

determining one or more maternal features of the at least one maternal wavelet transform modulus maxima;

evaluating each maternal feature of the one or more maternal features against one or more predetermined criteria to identify a plurality of candidate maternal peaks;

obtaining a set of windowed candidate maternal peaks, where each windowed candidate maternal peak in the set of windowed candidate maternal peaks is a window of a first number of samples around a candidate maternal peak of the plurality of candidate maternal peaks;

determining a set of template matching scores for the set of windowed candidate maternal peaks, wherein each template matching score of the set of template matching scores is found using a distance metric between each windowed candidate maternal peak of the set of windowed candidate maternal peaks and a maternal heart rate template;

determining a set of maternal peaks using a probabilistic likelihood search of the plurality of candidate maternal peaks that is based at least on the set of template matching scores;

updating one or more parameters of the maternal heart rate template based at least on the set of maternal peaks to create an updated maternal heart rate template; and determining an estimate of the maternal heart rate based on the set of maternal peaks and the updated maternal heart rate template.

10. A method for processing abdominal electrocardiogram signals comprising:

obtaining a combined electrocardiogram measurement of a maternal heart rate and a fetal heart rate, wherein the combined electrocardiogram measurement is sampled at a first sample rate;

transforming the combined electrocardiogram measurement into a wavelet domain to create a combined electrocardiogram measurement wavelet transform;

determining an estimate of the maternal heart rate from the combined electrocardiogram measurement wavelet transform;

removing the maternal heart rate from the combined electrocardiogram measurement wavelet transform using the estimate of the maternal heart rate to create a compensated combined electrocardiogram measurement wavelet transform;

identifying a fetal heart rate from the compensated combined electrocardiogram measurement wavelet transform, wherein identifying a fetal heart rate comprises:
  identifying at least one fetal wavelet transform modulus maxima in a particular detail level of a wavelet transform of the compensated combined electrocardiogram measurement wavelet transform,
  determining one or more fetal features of the at least one fetal wavelet transform modulus maxima,
  evaluating each fetal feature of the one or more fetal features against one or more predetermined criteria to identify a plurality of candidate fetal peaks,
  determining a set of preliminary fetal peaks using a probabilistic likelihood search of the plurality of candidate fetal peaks,
  determining a kurtosis score and a signal score of each preliminary fetal peak in the set of preliminary fetal peaks for a given time step, and
  selecting a set of final fetal peaks with kurtosis scores in a first predetermined range and signal scores in a second predetermined range; and displaying an indication of a final fetal heart rate based on the set of final fetal peaks.

11. The method of claim 10, wherein the combined electrocardiogram measurement is processed entirely in a wavelet transform domain to determine the maternal heart rate and the final fetal heart rate.

12. The method of claim 11, wherein the wavelet transform domain uses a Symmlets 4 wavelet as a mother wavelet.

13. The method of claim 10, wherein the particular detail level is detail level two of a four level wavelet transform.

14. The method of claim 10, further comprising creating an updated probability density of the maternal heart rate by updating an estimated mean value of the maternal heart rate.

15. The method of claim 10, wherein the one or more fetal features of the at least one fetal wavelet transform modulus maxima comprises at least one of a peak amplitude feature, a distance-from-mean feature, a peak-to-peak distance feature, a Lipschitz exponent feature, or a template matching feature.

16. The method of claim 10, wherein the one or more predetermined criteria is a threshold on each fetal feature of the one or more fetal features of the at least one fetal wavelet transform modulus maxima.

17. The method of claim 10, further comprising creating an updated probability density of the fetal heart rate by updating an estimated mean value of the fetal heart rate.

18. The method of claim 10, wherein determining the estimate of the maternal heart rate from the combined electrocardiogram measurement wavelet transform comprises:
  identifying at least one maternal wavelet transform modulus maxima in a first detail level of the combined electrocardiogram measurement wavelet transform;
  determining one or more maternal features of the at least one maternal wavelet transform modulus maxima;
  evaluating each maternal feature of the one or more maternal features against one or more predetermined criteria to identify a plurality of candidate maternal peaks;
  obtaining a set of windowed candidate maternal peaks, where each windowed candidate maternal peak in the set of windowed candidate maternal peaks is a window of a first number of samples around a candidate maternal peak of the plurality of candidate maternal peaks;
  determine a set of template matching scores for the set of windowed candidate maternal peaks, wherein each template matching score of the set of template matching scores is found using a distance metric between each windowed candidate maternal peak of the set of windowed candidate maternal peaks and a maternal heart rate template;
  determine a set of maternal peaks using a probabilistic likelihood search of the plurality of candidate maternal peaks that is based at least on the set of template matching scores;
  update one or more parameters of the maternal heart rate template based at least on the set of maternal peaks to create an updated maternal heart rate template; and
  determine an estimate of the maternal heart rate based on the set of maternal peaks and the updated maternal heart rate template.

19. An abdominal electrocardiogram processing computer system for determining a fetal heart rate of a fetus in a pregnant woman, the computer system comprising:

one or more processors; and
one or more computer-readable media having stored thereon executable instructions that when executed by the one or more processors configure the computer system to perform at least the following:
   obtain a combined electrocardiogram measurement of a maternal heart rate and a fetal heart rate, wherein the combined electrocardiogram measurement is sampled at a first sample rate;
   transform the combined electrocardiogram measurement into a wavelet domain to create a combined electrocardiogram measurement wavelet transform;
   determine an estimate of the maternal heart rate from the combined electrocardiogram measurement wavelet transform, wherein determining the estimate of the maternal heart rate from the combined electrocardiogram measurement wavelet transform comprises:
      identifying at least one maternal wavelet transform modulus maxima in a first detail level of the combined electrocardiogram measurement wavelet transform,
      determining one or more maternal features of the at least one maternal wavelet transform modulus maxima,
      evaluating each maternal feature of the one or more maternal features against one or more predetermined criteria to identify a plurality of candidate maternal peaks,
      obtaining a set of windowed candidate maternal peaks, where each windowed candidate maternal peak in the set of windowed candidate maternal peaks is a window of a first number of samples around a candidate maternal peak of the plurality of candidate maternal peaks,
      determining a set of template matching scores for the set of windowed candidate maternal peaks, wherein each template matching score of the set of template matching scores is found using a distance metric between each windowed candidate maternal peak of the set of windowed candidate maternal peaks and a maternal heart rate template,
      determining a set of maternal peaks using a probabilistic likelihood search of the plurality of candidate maternal peaks that is based at least on the set of template matching scores,
      updating one or more parameters of the maternal heart rate template based at least on the set of maternal peaks to create an updated maternal heart rate template, and
      determining an estimate of the maternal heart rate based on the set of maternal peaks and the updated maternal heart rate template;
   remove the maternal heart rate from the combined electrocardiogram measurement wavelet transform using the estimate of the maternal heart rate to create a compensated combined electrocardiogram measurement wavelet transform;
   identify a fetal heart rate from the compensated combined electrocardiogram measurement wavelet transform, wherein identifying a fetal heart rate comprises:
      identifying at least one fetal wavelet transform modulus maxima in a particular detail level of a wavelet transform of the compensated combined electrocardiogram measurement wavelet transform,
      determining one or more fetal features of the at least one fetal wavelet transform modulus maxima,
      evaluating each fetal feature of the one or more fetal features against one or more predetermined criteria to identify a plurality of candidate fetal peaks,
      determining a set of preliminary fetal peaks using a probabilistic likelihood search of the plurality of candidate fetal peaks,
      determining a kurtosis score and a signal score of each preliminary fetal peak in the set of preliminary fetal peaks for a given time step, and
      selecting a set of final fetal peaks with kurtosis scores in a first predetermined range and signal scores in a second predetermined range; and
   display an indication of a final fetal heart rate based on the set of final fetal peaks.

20. The abdominal electrocardiogram processing computer system of claim 19, wherein one or more computer-readable media further have stored thereon instructions that are executable by the one or more processors to configure the abdominal electrocardiogram processing computer system to perform at least the following:
   obtain a second combined electrocardiogram measurement of the maternal heart rate and the fetal heart rate, wherein the second combined electrocardiogram measurement of the maternal heart rate is sampled at the first sample rate;
   determine a second estimate of the maternal heart rate from a wavelet transform of the second combined electrocardiogram measurement using at least the updated maternal heart rate template;
   remove the maternal heart rate from the wavelet transform of the second combined electrocardiogram measurement using the second estimate of the maternal heart rate to create a second compensated electrocardiogram wavelet transform; and
   determine a second fetal heart rate from the second compensated electrocardiogram wavelet transform.

* * * * *